United States Patent [19]

Dhand et al.

[11] Patent Number: 5,741,689
[45] Date of Patent: Apr. 21, 1998

[54] METHODS TO INHIBIT SERINE KINASE ACTIVITY AND TO ALTER INTERSUBUNIT BINDING ACTIVITY OF PHOSPHATIDYLINOSITOL 3-KINASE, AND SERINE KINASE ACTIVE SEQUENCE OF THE SAME

[75] Inventors: Ritu Bala Dhand, London; Michael Derek Waterfield, Speen Newbury; Ian Donald Hiles, Bromley; Ivan Tarasovich Gout, London, all of England; Masato Kasuga; Kazuyoshi Yonezawa, both of Kobe, Japan; Peter End, London, England; Michael Fry, London, England; George Panayotou, London, England

[73] Assignee: Ludwig Institute for Cancer Research, New York, N.Y.

[21] Appl. No.: 185,424

[22] Filed: Jan. 21, 1994

[51] Int. Cl.$^6$ .................................................. C12N 9/12
[52] U.S. Cl. .............. 435/194; 435/240.27; 435/252.3; 435/320.1; 424/139.1; 530/24.1; 536/23.1; 536/24.1
[58] Field of Search .................... 435/194, 240.27, 435/320.1, 252.3; 536/23.1, 24.1; 530/387.9; 424/139.1

[56] References Cited

PUBLICATIONS

Otsu, M, et al. (1991) Cell 65, 91–104.

Dhand, et al., EMBO Journal vol. 13, No. 3, pp. 522–533, 1994, PI 3–kinase is a dual specificity enzyme: autoregulation by an intrinsic protein–serine kinase activity.

Dhand, et al, "EBMO Journal vol. 13, No. 3, 511–521, 1994, "PI 3–kinase: structural and functional analysis of inter–subunit interactions.

Carpenter, C.L., et al. (1993) Mol. Cell. Biol. 13(3), 1652–1665.

End, et al., J. Biol. Chem., vol. 268, No. 4, 10066–10075, (1993), "A Biosensor Approach to Probe the Structure and Function of the p85α Subunit of the phosphatidylinositol 3–kinase complex".

Reif, K., et al., J. Biol. Chem. 268, 10780–10788 (1993) "Divergent Regulation of Phosphatidylinositol 3–kinase p85α and p85β Isoforms upon T cell Activation".

Hiles, I., et al., Cell 70, 419–429 (1992), "Phosphatidyl–inositol 3–kinase: Structure and Expression of the 110 kd Catalytic Subunit".

Kaplan, et al., Cell, 50, 1021–1029 (1987) "Common Elements in Growth Factor Stimulation and Oncogenic Transformation: 85 kd phosphoprotein and Phosphatidylinositol Kinase Activity".

Carpenter, et al., J. Biol. Chem. 268, 9478–83 (1993), "A Tightly Associated Serine/Threonine Protein Kinase Regulates Phosphoinositide 3–kinase activity".

Carpenter, et al., J. Biol. Chem. 265, 19704–19711 (1990) "Purification and Characterization of Phosphoinositide 3–kinase from Rat Liver".

*Primary Examiner*—Charles L. Patterson, Jr.
*Attorney, Agent, or Firm*—Felfe & Lynch

[57] ABSTRACT

The invention provides for a method to inhibit the binding between the p85 and p110 subunits of said PI3-kinase and thus a method to modulate PI3-kinase activity and modulate the response of cells to external stimuli. In particular, disabling, by conventional means, residues located in the inter-SH2 domain of said p85 subunit, specifically a region containing amino acid residue 478 to amino acid residue 513 of p85α subunit, or amino acid residue 445 to amino acid residue 485 of p85β subunit of said PI3-kinase. Interference with these binding regions will affect binding between the subunits and results in inhibiting PI3-kinase activity. This invention further relates to a methods to modulate the serine kinase activity of the PI3-kinase which can be achieved by disabling the DRHNSN sequence of the p110 subunit and can also be used to effect changes in overall PI3-kinase activity. This invention is further related to an (ant)agonist which affects serine kinase activity of PI3-kinase. An agonist is provided which stimulates the phosphorylation of the p85 subunit at the serine residue at position 608, wherein phosphorylation at the serine residue indirectly results in inhibiting PI3-kinase activity.

28 Claims, 31 Drawing Sheets

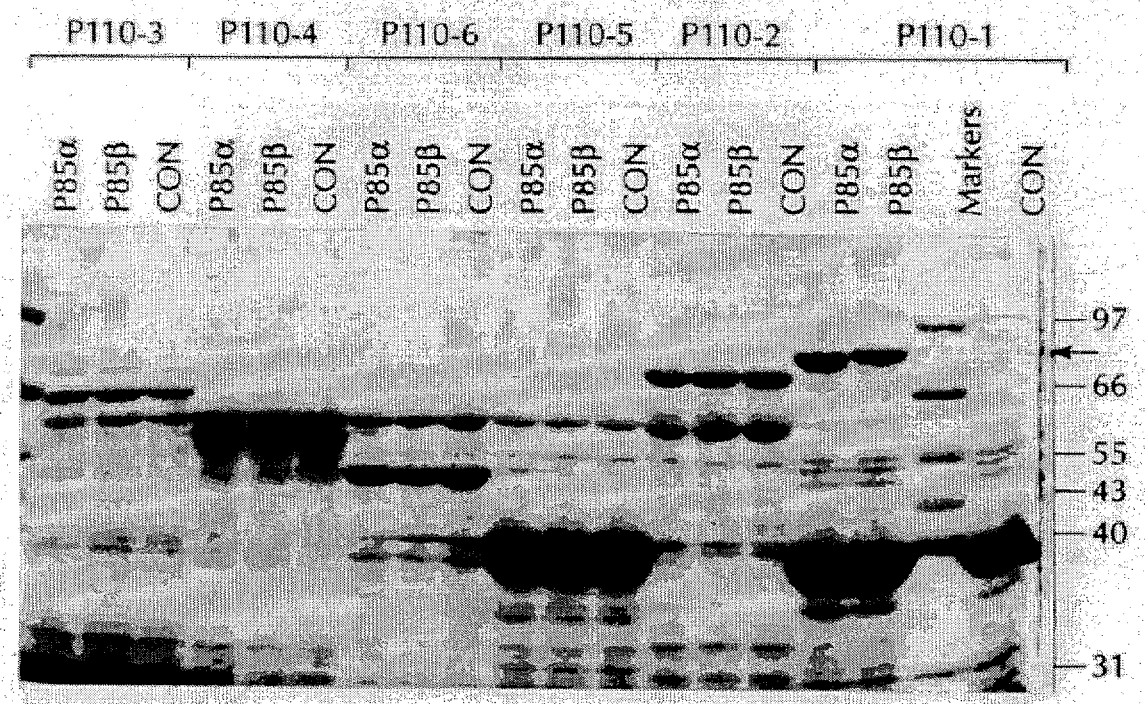

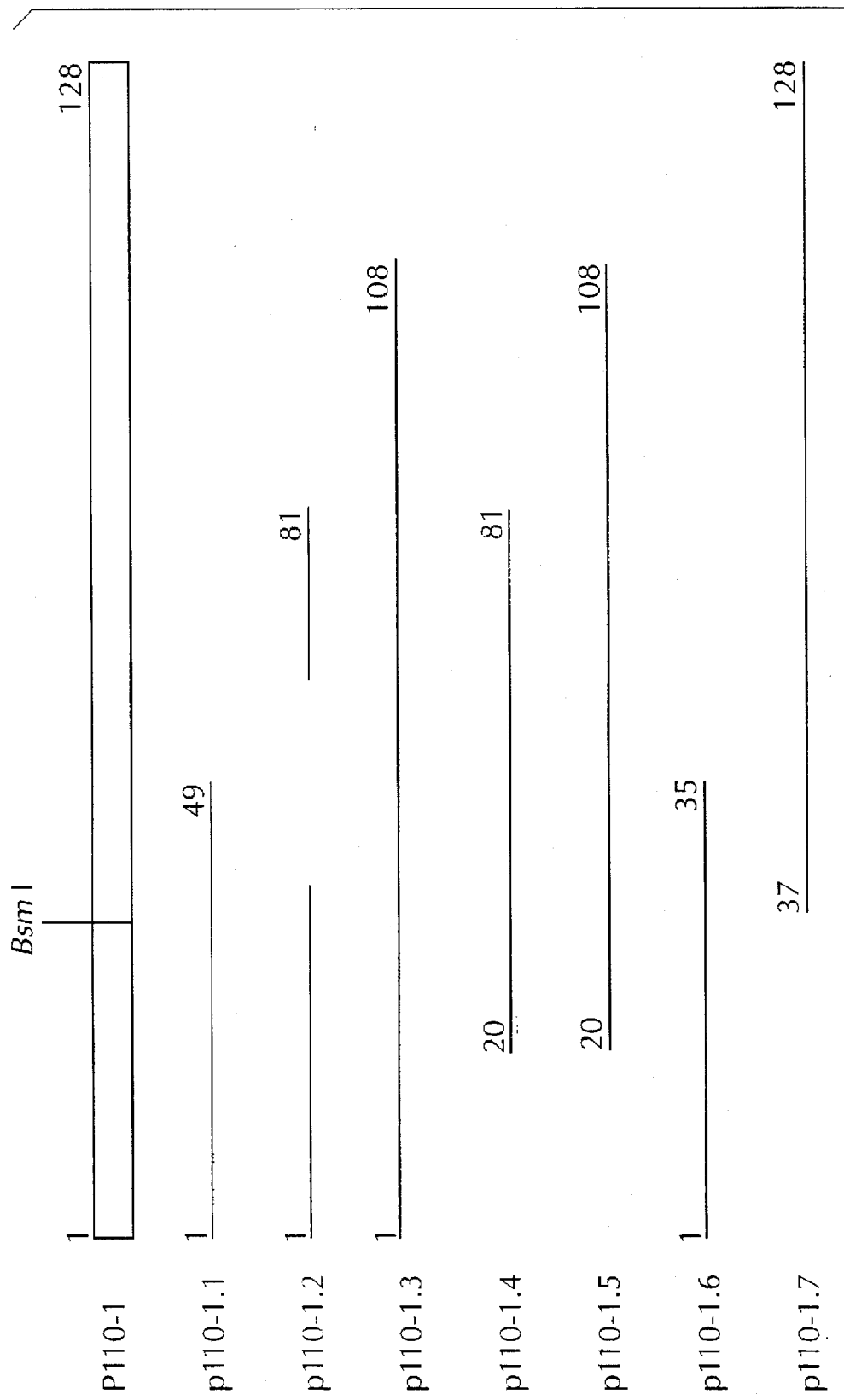

FIG. 9A

```
          431           446   453   460   474   481   488   495   502   509
           |             |     |     |     |     |     |     |     |     |
            1st SH2 domain    GABCDEFGABCDEFGABCDEFGABCDEFGABCDEFGABCDEFGABCDEFGA
p85α ..NESLAQYNPKLDVKLLYPVSKYQQDQVVKEDNIEAVGKKLHEYNTQFQEKSREYDRLYEDYTRTSQEIQMKRTAIEAFNETIKIFEEQCQTQERYSKEYIEKFKREGN
p85β ..HESLAQYNAKLDTRLLYPVSKYQQDQIVKEDSVEAVGAQLKVHQQYQDKSREYDQLYEEYTRTSQELQMKRTAIEAFNETIKIFEEQGQTQEKCSKEYLERFRREGN 518   525   532   539   546   553   560   567   574   581   588        607                   620
   |     |     |     |     |     |     |     |     |     |     |          |                     |
   efgabcdefgabcdefgabcdefgabcdefgabcdefgabcde                                                 2nd SH2
p85α ETEIQRIMHNYEKLKSRISEIVDSRRLEEDLKKQAAEYREIDKRMNSIKPDLIQLRKTRDQYLMWLTQKGVRQKKLINEWLGN-ENTEDQYSLVEDDEDLPHHDEKTWN.
p85β EKEMQRILLNSERLKSRIAEIHESRTKLEQELRAQASDNREIDKRMNSLKPDLMQLRKIRDQYLVWLTQKGARQKKINEWLGIKNETEDQYSLMEDEDDLPHHEERTWY.
```

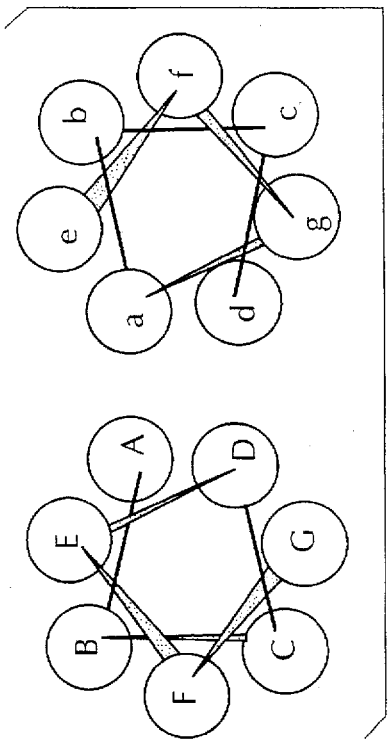

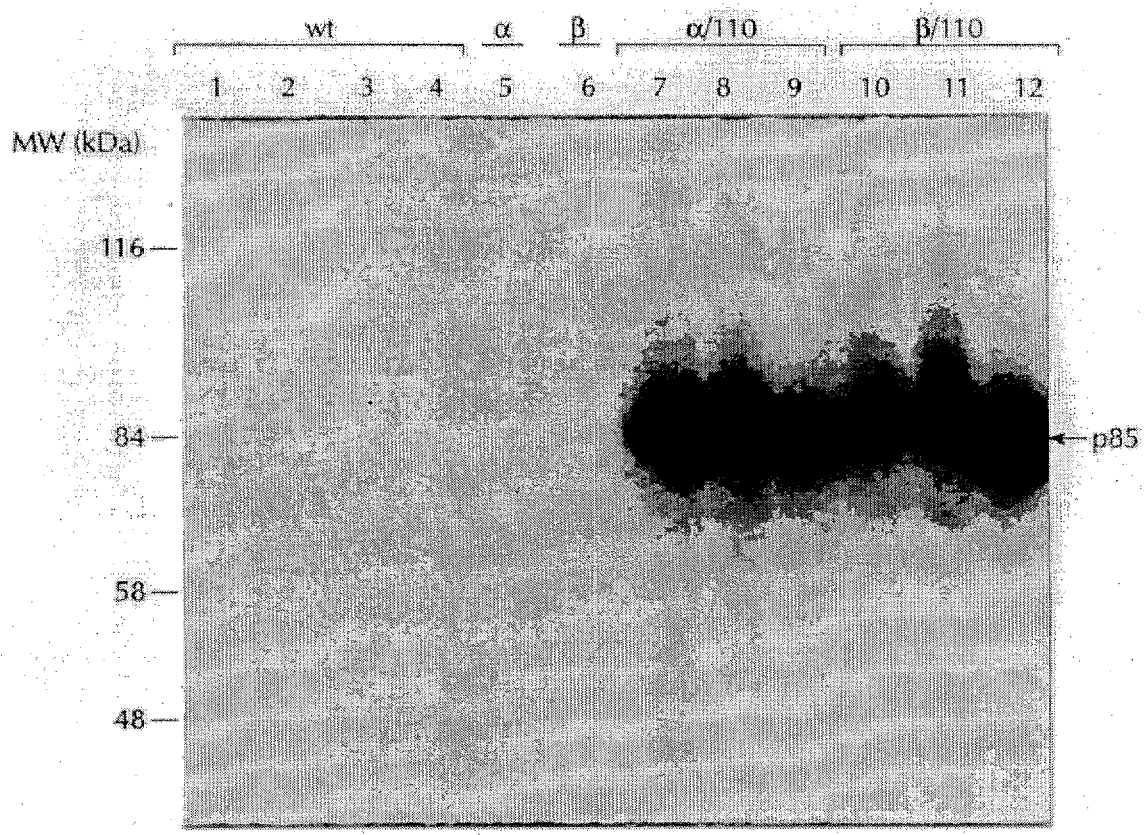

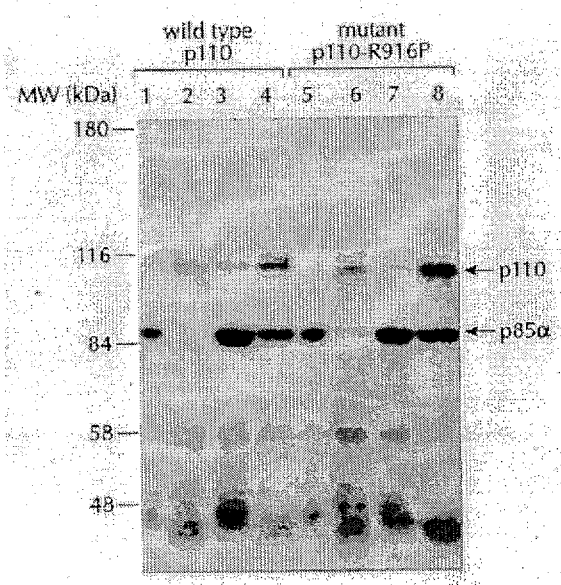
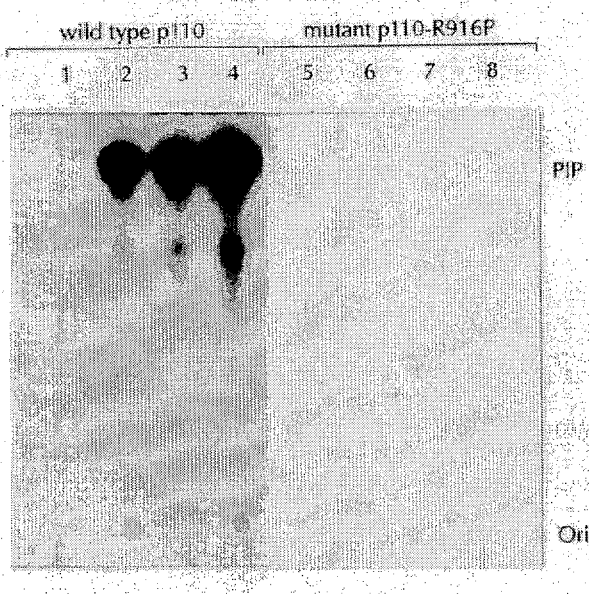
FIG. 13A
FIG. 13B

FIG. 14A

MW (kDa)
180—
116—
84—  ← GST-p85α
       ← p85α
58—
48—

FIG. 14B

MW (kDa)
180—
116—
84—  ← GST-p85α
       ← p85α
58—
48—

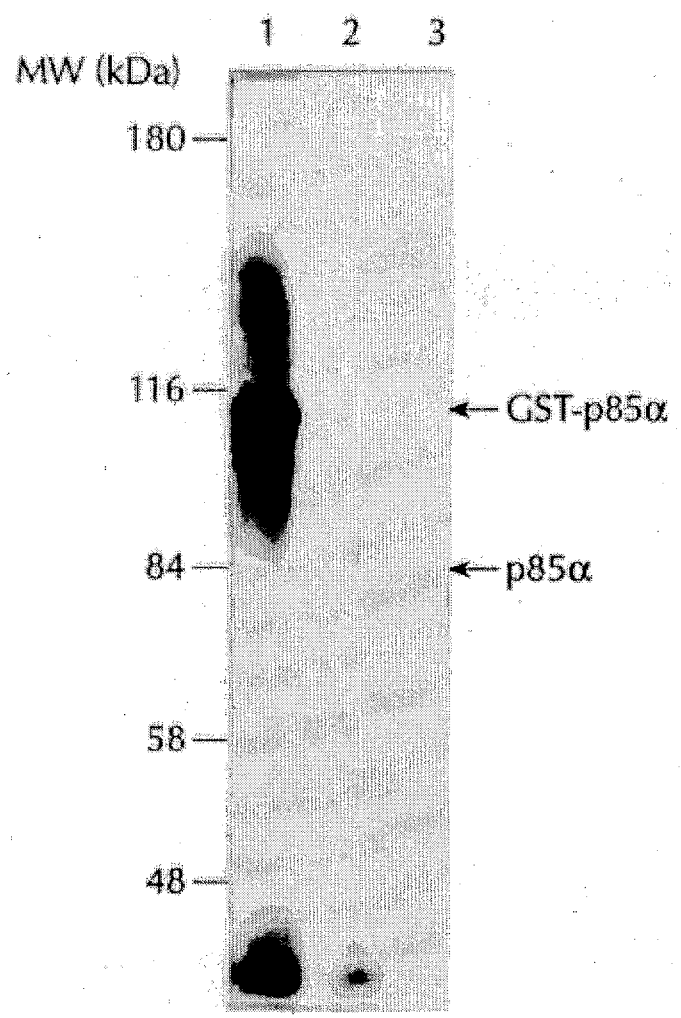

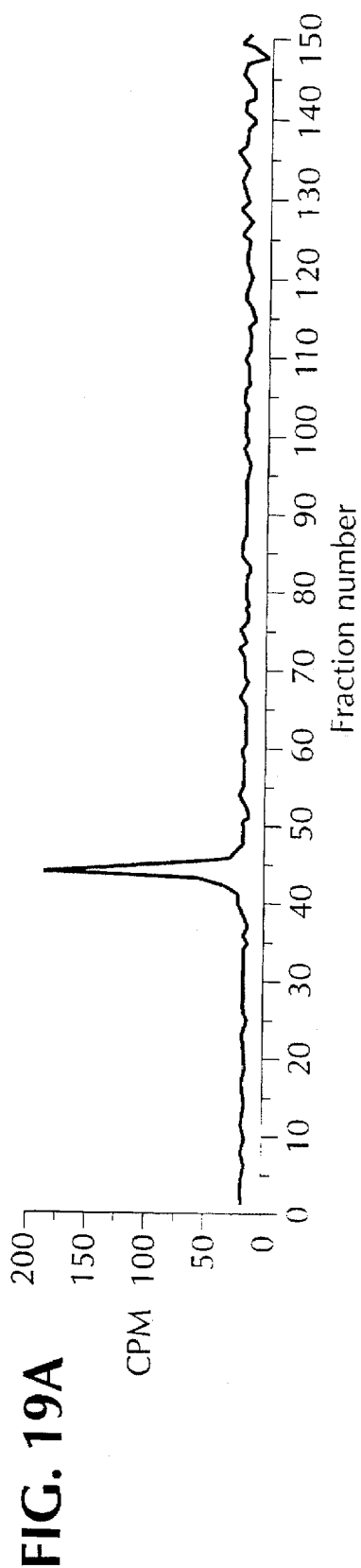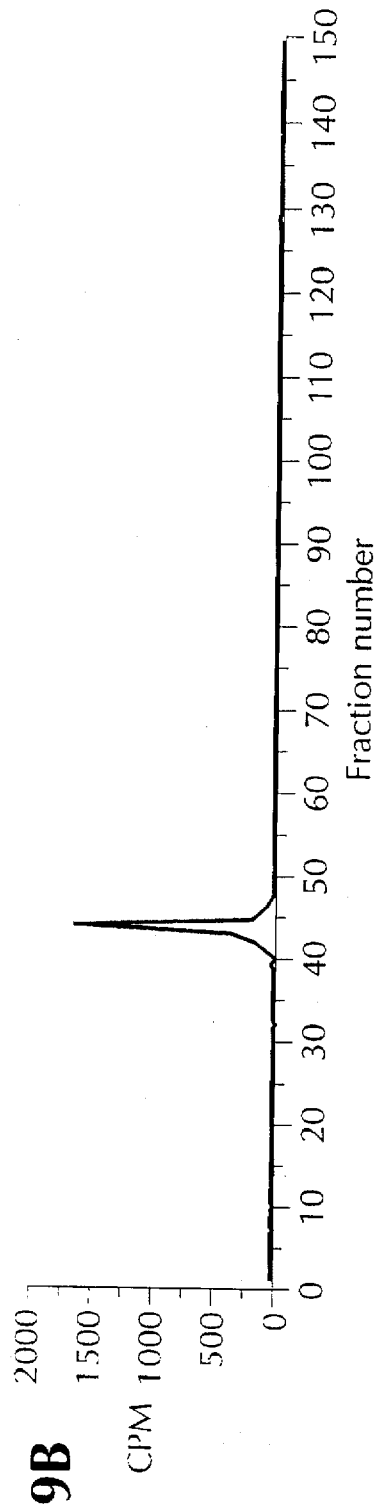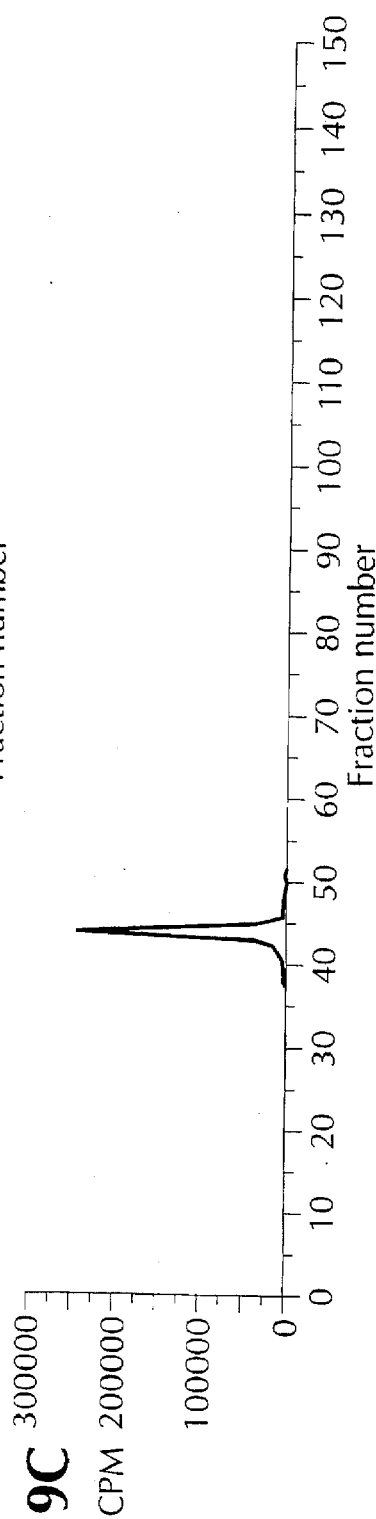

SEQUENCE LISTING ( 1 ) GENERAL INFORMATION:

( i i i ) NUMBER OF SEQUENCES: 5

( 2 ) INFORMATION FOR SEQ ID NO: 1:

( i ) SEQUENCE CHARACTERISTICS:
      ( A ) LENGTH: 216 amino acid residues
      ( B ) TYPE: amino acid
      ( D ) TOPOLOGY: linear ( x i ) SEQUENCE DESCRIPTION: SEQ ID NO: 1:

```
Asn  Glu  Ser  Leu  Ala  Gln  Tyr  Asn  Pro  Lys  Leu  Asp  Val  Lys  Leu  Leu
                    5                        10                       15

Tyr  Pro  Val  Ser  Lys  Tyr  Gln  Gln  Asp  Gln  Val  Val  Lys  Glu  Asp  Asn
                    20                       25                       30

Ile  Glu  Ala  Val  Gly  Lys  Lys  Leu  His  Glu  Tyr  Asn  Thr  Gln  Phe  Gln
                    35                       40                  45
```

```
Glu  Lys  Ser  Arg  Glu  Tyr  Asp  Arg  Leu  Tyr  Glu  Asp  Tyr  Thr  Arg  Thr
     50                       55                      60

Ser  Gln  Glu  Ile  Gln  Met  Lys  Arg  Thr  Ala  Ile  Glu  Ala  Phe  Asn  Glu
65                       70                      75                           80

Thr  Ile  Lys  Ile  Phe  Glu  Glu  Gln  Cys  Gln  Thr  Gln  Glu  Arg  Tyr  Ser
                    85                      90                           95

Lys  Glu  Tyr  Ile  Glu  Lys  Phe  Lys  Arg  Glu  Gly  Asn  Glu  Thr  Glu  Ile
                    100                     105                     110

Gln  Arg  Ile  Met  His  Asn  Tyr  Glu  Lys  Leu  Lys  Ser  Arg  Ile  Ser  Glu
               115                     120                     125

Ile  Val  Asp  Ser  Arg  Arg  Arg  Leu  Glu  Glu  Asp  Leu  Lys  Lys  Gln  Ala
          130                     135                     140

Ala  Glu  Tyr  Arg  Glu  Ile  Asp  Lys  Arg  Met  Asn  Ser  Ile  Lys  Pro  Asp
145                          150                     155                     160

Leu  Ile  Gln  Leu  Arg  Lys  Thr  Arg  Asp  Gln  Tyr  Leu  Met  Trp  Leu  Thr
                    165                     170                     175

Gln  Lys  Gly  Val  Arg  Gln  Lys  Lys  Leu  Asn  Glu  Trp  Leu  Gly  Asn  Glu
                    180                     185                     190

Asn  Thr  Glu  Asp  Gln  Tyr  Ser  Leu  Val  Glu  Asp  Asp  Glu  Asp  Leu  Pro
               195                     200                     205

His  His  Asp  Glu  Lys  Thr  Trp  Asn
     210                     215
```

( 2 ) INFORMATION FOR SEQ ID NO: 2:

( i ) SEQUENCE CHARACTERISTICS:
        ( A ) LENGTH: 217 amino acid residues
        ( B ) TYPE: amino acid
        ( D ) TOPOLOGY: linear ( x i ) SEQUENCE DESCRIPTION: SEQ ID NO: 2:

```
His  Glu  Ser  Leu  Ala  Gln  Tyr  Asn  Ala  Lys  Leu  Asp  Thr  Arg  Leu  Leu
                    5                       10                      15

Tyr  Pro  Val  Ser  Lys  Tyr  Gln  Gln  Asp  Gln  Ile  Val  Lys  Glu  Asp  Ser
          20                       25                      30

Val  Glu  Ala  Val  Gly  Ala  Gln  Leu  Lys  Val  Tyr  His  Gln  Gln  Tyr  Gln
          35                       40                      45

Asp  Lys  Ser  Arg  Glu  Tyr  Asp  Gln  Leu  Tyr  Glu  Glu  Tyr  Thr  Arg  Thr
     50                       55                      60

Ser  Gln  Glu  Leu  Gln  Met  Lys  Arg  Thr  Ala  Ile  Glu  Ala  Phe  Asn  Glu
65                       70                      75                           80

Thr  Ile  Lys  Ile  Phe  Glu  Glu  Gln  Gly  Gln  Thr  Gln  Glu  Lys  Cys  Ser
                    85                      90                           95

Lys  Glu  Tyr  Leu  Glu  Arg  Phe  Arg  Arg  Glu  Gly  Asn  Glu  Lys  Glu  Met
                    100                     105                     110

Gln  Arg  Ile  Leu  Leu  Asn  Ser  Glu  Arg  Leu  Lys  Ser  Arg  Ile  Ala  Glu
               115                     120                     125

Ile  His  Glu  Ser  Arg  Thr  Lys  Leu  Glu  Gln  Glu  Leu  Arg  Ala  Gln  Ala
          130                     135                     140

Ser  Asp  Asn  Arg  Glu  Ile  Asp  Lys  Arg  Met  Asn  Ser  Leu  Lys  Pro  Asp
145                          150                     155                     160

Leu  Met  Gln  Leu  Arg  Lys  Ile  Arg  Asp  Gln  Tyr  Leu  Val  Trp  Leu  Thr
                    165                     170                     175

Gln  Lys  Gly  Ala  Arg  Gln  Lys  Lys  Ile  Asn  Glu  Trp  Leu  Gly  Ile  Lys
                    180                     185                     190
```

(2) INFORMATION FOR SEQ ID NO: 3:

(i) SEQUENCE CHARACTERISTICS:
        (A) LENGTH: 6 amino acid residues
        (B) TYPE: amino acid
        (D) TOPOLOGY: linear (xi) SEQUENCE DESCRIPTION: SEQ ID NO: 3:

Asp Arg His Asn Ser Asn
                    5

(2) INFORMATION FOR SEQ ID NO: 4:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO: 4:

TGGGAATTGG GGATCCTCAC AATAGTA     27

(2) INFORMATION FOR SEQ ID NO: 5:

(i) SEQUENCE CHARACTERISTICS:
        (A) LENGTH: 30 amino acid residues
        (B) TYPE: amino acid
        (D) TOPOLOGY: linear (xi) SEQUENCE DESCRIPTION: SEQ ID NO: 5:

Lys Leu Asn Glu Trp Leu Gly Asn Glu Asn Thr Glu Asp Gln Tyr Ser
            5                      10                  15

Leu Val Glu Asp Asp Glu Asp Leu Pro His His Asp Glu Lys
          20                    25                  30

(Preceding sequence continuation:)

Asn Glu Thr Glu Asp Gln Tyr Ser Leu Met Glu Asp Glu Asp Asp Leu
      195                    200                    205

Pro His His Glu Glu Arg Thr Trp Tyr
    210                    215

METHODS TO INHIBIT SERINE KINASE ACTIVITY AND TO ALTER INTERSUBUNIT BINDING ACTIVITY OF PHOSPHATIDYLINOSITOL 3-KINASE, AND SERINE KINASE ACTIVE SEQUENCE OF THE SAME

FIELD OF THE INVENTION

The invention relates to the discovery of a method to inhibit the binding between the p110 and p85 subunits of phosphatidyl-inositol 3-kinase (hereinafter "PI3-kinase"). This discovery provides a method to modulate PI3-kinase activity and modulates the response of cells to external stimuli. In particular, disabling, by conventional means, residues located in the inter-SH2 domain of the p85 subunit interferes with the binding activity between the subunits and results in modulating PI3-kinase activity.

The invention further relates to a serine kinase active sequence of PI3-kinase and a method to modulate the serine kinase activity of the PI3-kinase which can be achieved by disabling the DRHNSN sequence of the p110 subunit. This method can be used to affect overall PI3-kinase activity.

In addition, an agonist is provided which stimulates the phosphorylation of the p85 subunit at the serine residue at position 608, wherein phosphorylation at the serine residue results in inhibiting PI3-kinase activity.

This invention further relates to agonist and antagonist molecules to activity of PI3-kinase.

BACKGROUND OF THE INVENTION

Major advances have taken place in our knowledge of the structure and function of the signal transducing molecules and second messenger systems coupled to the cell surface receptors. A subset of polypeptide growth factor receptors belong to the family of protein tyrosine kinases and activation of these receptors following ligand binding involves autophosphorylation of the receptor as well as phosphorylation of a number of intracellular substrate proteins (reviewed in Ullrich, A et al., 1990). The importance of receptor autophosphorylation had been unclear until recently, when evidence from several laboratories has suggested that this event may mediate the formation of complexes between receptor proteins and putative growth regulator proteins such as phospholipase Cγ(PLCγ) (Meisenhelder et al, 1989), phosphatidylinositol PI3-kinase (Coughlin, S. R. et al. 1989). GTPase-activating protein (GAP) (Kaplan et al., 1990), the serine/threonine kinase Raf (Morrison et al. 1989), and members of the src-family of protein tyrosine kinases (Kypta, R M et al., 1990) (reviewed in Cantley, L C et al., 1991)

The association of PI kinase activity with activated receptors is of interest because of the increased turnover of PI and its phosphorylated derivatives have been implicated in the action of hormones, growth factors and transformation of cells by DNA and RNA viruses (reviewed in Whitman, M et al., 1988; Cantley et al., 1991).

Several classes of PI kinase are known to exist. Fibroblasts contain at least two PI kinase activities which are distinguishable based on their detergent sensitivity and kinetic properties (Whitman, M et al., 1987). These two activities are classified as Type I (inhibited by non-ionic detergents) and Type II (stimulated by non-ionic detergents and inhibited by adenosine). A third distinct species (Type III) has been identified in bovine brain but remains poorly characterized (Enderman, G et al., 1987). One class of PI kinase activity in particular has become of major interest in the search for second messenger systems linked to protein tyrosine kinases because this activity was shown to co-immunoprecipitate with activated platelet-derived growth factor (PDGF) receptors (Kaplan, D R et al., 1987; Coughlin, S R et al., 1989) and with the polyoma middle T antigen/pp60$^{c-src}$ complex (Whitman, M. et al., 1985). This activity has been shown to be due to a Type I PI kinase which produces novel inositol lipids phosphorylated at the D-3 position of the inositol ring (Whitman, M. et al., 1988). More recently, this enzyme has also been shown to associate with the CSF-1 receptor, kit (Varticovski, L. et al., 1989), the epidermal growth factor (EGF) receptor (Bjorge et al., 1990), the PDGF alpha-receptor (Yu et al., 1991), the insulin receptor (Ruderman et al., 1990), the hepatocyte growth factor receptor, met (Graziani et al., 1991), and with activated non-receptor protein-tyrosine kinases (Fukui & Hanafusa, 1989; Chan et al., 1990, Varticovski et al., 1991).

PI3 kinase activity has been closely linked with the presence of 85 kD protein in the immunoprecipitates which can be phosphorylated on tyrosine residues by the associated protein-tyrosine kinase both in vitro and in vivo (Kaplan, D R et al., 1987; Courtneidge, S A et al., 1987; Cohen et al., 1990). A 650 fold purification of PI3-kinase from bovine brain was described which, among other proteins present in the purest preparation, contained an 85 kD protein which was shown to be an in vitro substrate for the PDGF and EGF receptors (Morgan S J et al., 1990). Using sequence information from tryptic peptides derived from this protein, two homologous bovine p85 proteins, denoted p85α and p85β (Otsu, M et al., 1991) have been cloned. Murine and human p85α homologues have been independently cloned using different strategies (Escobedo, J A et al., 1991; Skolnick, E Y et al., 1991). Both of these p85 proteins can be demonstrated to bind directly to phosphorylated PDGF receptor in vitro (Otsu, M et al., 1991; Escobedo, J A et al., 1991b). These proteins appear to function as the receptor binding subunits of the PI3-kinase activity when expressed in a variety of cell systems. However, immunoprecipitation of $^{125}$I-labelled bovine brain PI3-kinase with antibodies raised against p85 proteins precipitates an 85 Kd protein together with a second protein of 110 Kd molecular weight (Otsu, M et al., 1991).

PI3-kinase is one of a growing number of potential signalling proteins which associate with protein-tyrosine kinases activated either by ligand stimulation or as a consequence of cell transformation. PI3-kinase may also play a key role in intracellular signal processes linked directly or indirectly to diverse receptor types and in some cells may be an important mediator in the events which lead to mitogenesis (Fantl et al., 1992; Valius and Kazlauskas, 1993). PI3-kinase phosphorylates the D3 position of the inositol ring of PI and its phosphorylated derivatives to produce PI(3)P, PI(3,4)P2, and PI(3,4,5)P3. Rapid increases in the levels of PI(3,4)P2 and PI(3,4,5)P3 have been observed when quiescent cells are stimulated with peptide growth factors such as platelet-derived growth factor (PDGF) and epidermal (EGF).

For the above reasons and the potential uses of PI3-kinase modulation, experiments were conducted which determined the primary structure of the PI3-kinase in terms of its PI3-kinase activity, the intersubunit interactions between its p85 and the p110 subunits, and a novel serine kinase activity found to be intrinsic in the p110 subunit.

The discovery of the binding domains of the p85 and the p110 subunits and the novel protein serine kinase activity of the p110 subunit have great potential in studying the regulation of PI3-kinase activity.

Determination of the primary structure of the PI3-kinase has been fundamental towards the understanding of its role in signal transducing processes. Purified bovine PI3-kinase from brain or liver is a heterodimer of 85 and 110 kDa (Carpenter et al., 1990; Fry et al., 1992; Morgan et al., 1990; Shibasaki et al., 1991). Through cDNA cloning, two forms of p85, termed p85α and p85β, which lack catalytic activity have been described (Otsu, et al., 1991). Analysis of the primary sequence of p85 reveals a protein with a multidomain structure which contains a number of non-catalytic domains first described in studies of transforming proteins of the src family. At the N-terminus lies a Src homology region 3 domain (SH3) (reviewed in Pawson and Schlessinger, 1993) and adjacent to this is a region with significant sequence similarity to the product of the breakpoint cluster region gene BCR (Otsu et al., 1991). Since the BCR protein has a GAP activity for ras, this region of p85 may interact with small GTP binding protein (reviewed in Fry 1992). The C-terminal half of the molecule is dominated by two SH2 domains (reviewed in Pawson and Gish, 1992) that flank a region which has been predicted to adopt a helical conformation (Panayotou et al., 1992) The presence of these distinct functional domains suggests that the p85 proteins have multiple interactive and regulatory roles.

The modular structure of p85 has facilitated both structural and functional studies on this protein and has led to rapid advances in our understanding of its role in the PI3-kinase complex.

Until recently, very little was known regarding the p110 protein. Only a single form of p110 has been cloned to date and expression studies have clearly shown that this can alone encode a protein with a PI3-kinase activity. This work is described in Hiles et al., 1992, the contents of which are incorporated by reference in its entirety. The cloned p110 is homologous to Vps34p, a yeast PI3-kinase which is involved in vacuolar protein sorting (Herman and Emr, 1990; Schu et al., 1993). Analysis of p110 sequences reveals that redundant kinase motifs and sequence comparisons with Vps34p, and the more recently cloned Tor2, another putative yeast PI3-kinase homologue required for GI progression (Kunz et al., 1993) has allowed a catalytic domain to be assigned to the C-terminal region of the protein (Hiles et al., 1992). Sequence analysis of the N-terminal region of p110 reflects no significant homology to any known proteins, and this region may play a regulatory role.

PI3-kinase may be regulated by a series of events, such as translocation of PI3-kinase to cell membranes with consequent access to substrate, and the subsequent association with, and phosphorylation by, protein-tyrosine kinases (PTKs) (Reviewed in Panayotou and Waterfield, 1992). The binding of PI3-kinase through its SH2 domains to phosphotyrosine-containing sequences on PTKs is able to independently bring about some degree of activation of the enzyme. Tyrosine phosphorylated peptides corresponding to potential PI3-kinase sites on the insulin receptor substrate, IRS-1, or the intact IRS-1 protein have been shown to activate PI3-kinase in vivo (Backer et al., 1992; Giorgetti et al., 1993) Similarly, addition of a phosphotyrosine-containing peptide corresponding to $Y_{751}$ of the PDGFB receptor, a known in vivo binding site, also causes activation of PI3-kinase in vitro (Carpenter et al., 1993). Further, it has been shown that upon binding this $Y_{751}$-phosphopeptide, the p85 subunit of the PI3 kinase and its N-terminal SH2 domain in particular, undergo a conformational change (Panayotou et al., 1992). This induced change in conformation of the p85 protein may be transmitted to the associated p110 subunit and thus contribute to its activation.

Since p85 binds receptor through its SH2 domains, regulation of enzymatic activities intrinsic to the associated catalytic subunit can result from physical translocation of the enzyme to the membrane with access to substrate or by interactions between the subunits which result in the activation of the PI3-kinase activity intrinsic to the p110 subunit.

There is also another mechanism which involves changes induced in the p85 protein upon binding to PTKs, which are then transmitted to the associated catalytic domain and result in its activation. Such a change has been detected when the p85 subunit of PI3-kinase and in particular, its N-terminal SH2 domain binds to a phosphotyrosine-containing peptide corresponding to $Y_{751}$ of the PDGF B-receptor, the novel PI3-kinase binding site (Panayotou et al., 1992).

It has also been discovered that phosphorylation on the p85 or the p110 subunit, for example on tyrosine, serine or threonine residues can regulate kinase activity. Consistent with the concept that tyrosine phosphorylation of PI3-kinase by an activated PTK can cause an increased PI3-kinase activity, is the report that a decrease in PI3-kinase activity follows treatment of the enzyme with a phosphotyrosyl protein phosphatase (Ruiz-Larrea et al., 1993)

Serine and threonine phosphorylation of the components of the PI3-kinase complex may also play a role in regulation of the enzyme as several studies have shown that the p85α subunit of the PI3-kinase immunoprecipitated from quiescent cells is phosphorylated on serine and threonine residues (Kaplan et al., 1987; Reif et al., 1993; Roche et al., 1993). The purified bovine brain preparation of PI3-kinase has been shown to copurify with an associated protein serine kinase activity and a recent report from Carpenter et al, 1993, showed that a similar activity, which is termed PIK kinase, may copurify with and regulate rat liver PI3-kinase.

Experiments have been carried out to elucidate the nature of the associated protein-serine kinase and its possible role in the regulation of PI3-kinase. Specifically, wild-type and mutant recombinant PI3-kinase subunits alone or in complex show that the p110 subunit of PI3-kinase has both an intrinsic phosphoinositide kinase activity and a protein-serine kinase activity with unique specificity for p85. Furthermore, a high stoichiometry of phosphorylation establishes a single serine phosphorylation site on the p85 protein.

A method to inhibit PI3-kinase activity through manipulation of the protein serine kinase activity associated with PI3-kinase is provided herein. An agonist and antagonist of the associated protein serine kinase activity is also provided.

A method by which to manipulate the interaction between the regulatory p85 subunit and the p110 catalytic domain has been developed which provides a means to modulate PI3-kinase activity.

One of the principal objects of this invention is to provide a method to manipulate the interaction between the p85 and p110 subunits to modulate PI3-kinase activity. In particular, blocking the association or binding between p85 and the p110 subunits provides a means for regulating downstream signal transduction pathways.

Identification of the binding sites also aid in assaying for inhibitors, i.e., antagonists, of this interaction. Antagonists which interfere with the interaction between the p85 and 'p110 subunits are also provided for herein. These antagonists typically bind to, interact, or otherwise associate with critical regions of the p85 subunit which prevents binding with its p110 subunit. The use of these antagonists result in preventing the interaction between the p85 and p110 subunits and further result in loss of catalytic activity.

In addition, these antagonists can be utilized to detect the presence of a subunit of the PI3-kinase through competitive binding assays.

It is also an object of this invention to provide for expression vectors containing the nucleic acid molecules which code for the antagonists described herein. It is a further object of this invention to provide for host cells which are transfected with the above expression vectors.

Further provided herein is a method to inhibit PI3-kinase activity by manipulation of a novel intrinsic protein-serine kinase activity which is detectable only upon high affinity binding of the p110 subunit with its substrate, the p85 subunit.

A method for treating subjects suffering from pathological conditions characterized by insufficient PI3-kinase activity comprising treatment with pharmaceutical compositions containing an agonist to increase PI3-kinase activity.

SUMMARY OF THE INVENTION

The invention further relates to the discovery of a method to inhibit the binding between the p110 and p85 subunits of said PI3-kinase. This discovery provides for a method to modulate PI3-kinase activity and also modulates the response of cells to external stimuli. In particular, disabling, by conventional means, residues located in the inter-SH2 domain of said p85 subunit, specifically a region containing amino acid residue 478 to amino acid residue 513 of p85α subunit, and residues from amino acid 445 to amino acid residue 485 of p85β subunit of said PI3-kinase, result in loss of serine kinase activity. Interference with these binding regions, in the form of antagonistic molecules, also affects binding between the subunits and results in inhibiting PI3-kinase activity. In particular, antibodies which bind to the critical regions can interfere with binding between the subunits.

Methods to modulate the serine kinase activity of the PI3-kinase can be achieved by disabling or otherwise interfering with the DRHNSN sequence of the p110 subunit and can be used to effect changes in overall PI3-kinase activity.

BRIEF DESCRIPTION OF THE DRAWINGS

FIG. 1Aii shows PI3 kinase assays performed on immunoprecipitates from Sf9 cells.

FIG. 1Bii presents results of PI3-kinase assays following immunoprecipitation of recombinant p110.

FIG. 1Biii shows detection of p85α, bound to p110, via Coomassie Blue staining, using SDS-PAGE.

FIG. 7B shows results of a PI3 kinase assay on these molecules.

FIGS. 8A and 8B repeat 7A and 7B, using different fusion proteins.

FIGS. 9A, 9B, 9C and 9D compare the amino acid sequences of p85α and p85β.

FIG. 11 shows autoradiographic studies of p85α and p85β, using SDS-PAGE and $Mn^{2+}$ dependent protein kinase activity assays.

FIG. 12Cii is phosphoamino analysis of p110.

FIG. 13A presents results of mutagenesis experiments on p110.

FIG. 13B is a protein kinase assay on this protein.

FIG. 14A shows that p85α, when complexed with wild type p110, phosphorylates in vitro.

FIG. 14B shows that p110 exhibits trans-kinase activity.

FIG. 14C shows that GST p85α, alone, has no associated protein kinase activity.

DETAILED DESCRIPTION OF THE INVENTION

Figure 1A:
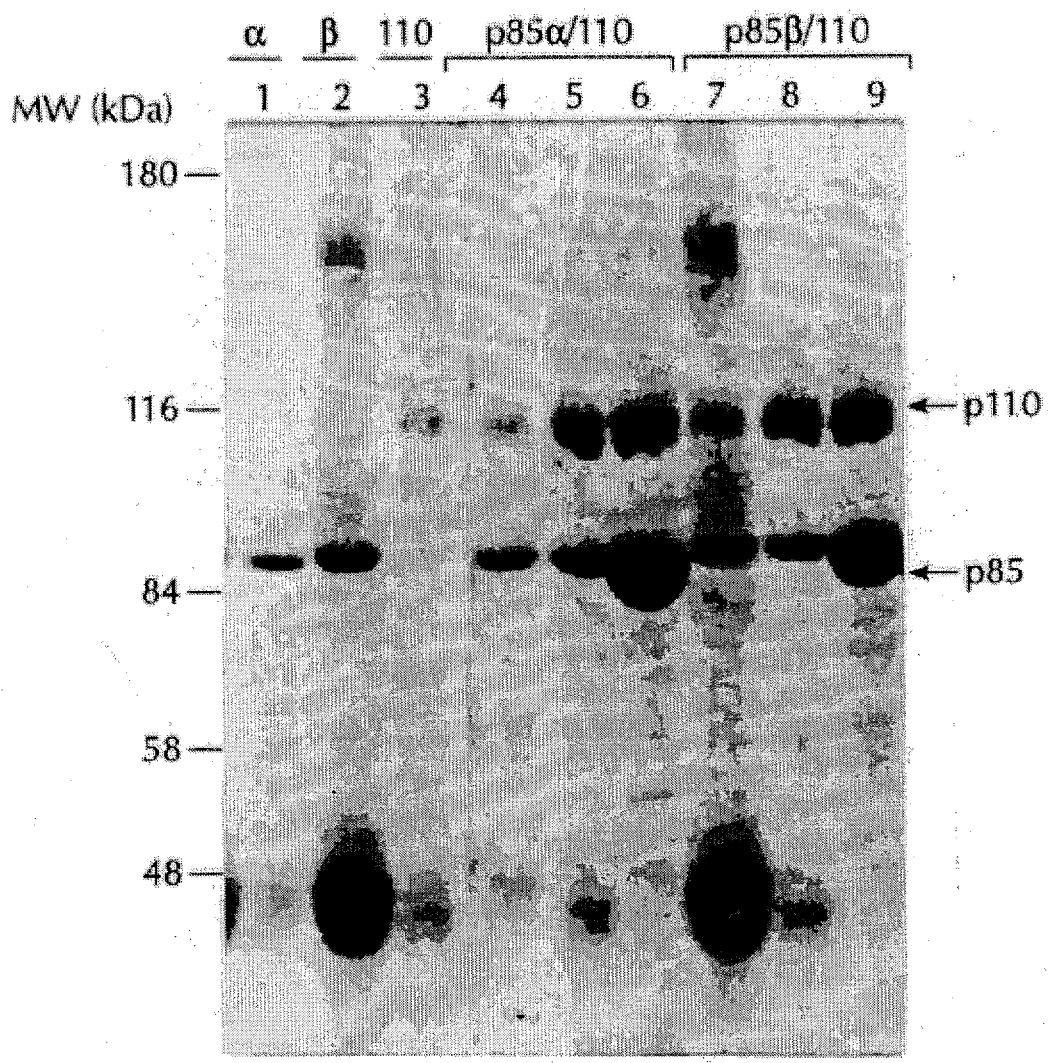
FIG. 1Ai shows SDS-PAGE analysis of recombinant p85α, p85β and p110 produced in Sf9 cells.
Figure 1B:
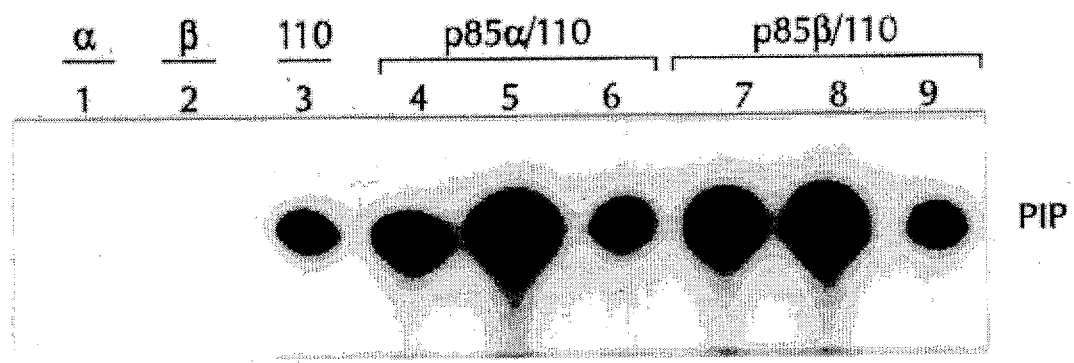
FIG. 1Bi shows binding of p85α and p85β to p110, using Coomassie Blue staining.
Figure 1C:
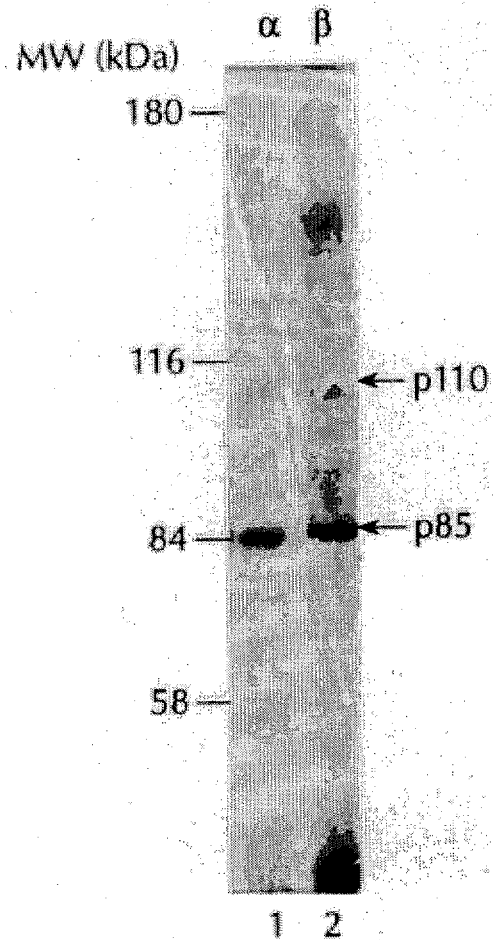
Figure 1D:
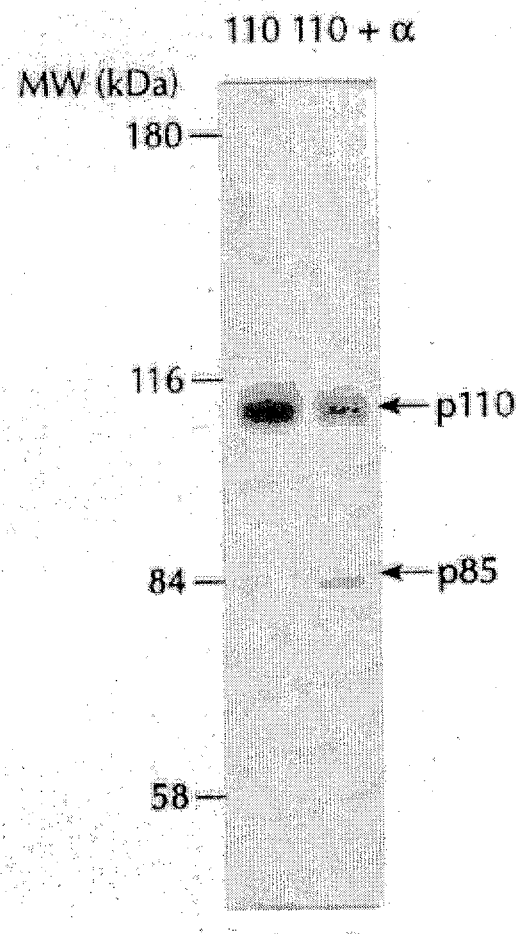
Figure 1E:
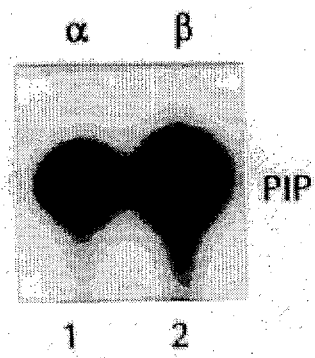

The examples which follow, show that the p110 subunit can reconstitute with p85α or p85β to form active PI3-kinase complexes. After establishing that binding between the subunits takes place, it was determined that the inter-SH2 region of p85α is required for binding to p110. By carrying out mapping experiments to ascertain the precise site of binding, a region within the inter-SH2 region was found to be responsible for inter-subunit interaction. The specific site for p85 binding on p110 and the structure of the inter-SH2 region of p85 were also elucidated, as described supra.

With the knowledge of the p85/p110 binding region, it is possible now to provide mechanisms to interfere with binding in order to regulate, modulate or otherwise control or affect PI3-kinase activity. In the absence of binding, the following experiments show that PI3-kinase activity is not measurable. See Dhand et al., paper, entitled "PI3-kinase: Structural and functional analysis of intersubunit interactions" (hereinafter "Intersubunit Interactions"), EMBO Journal, Vol.13, No.3, (Feb. 1, 1994), 511–521, the content of which is incorporated herein by reference, in its entirety. In addition, with the knowledge of the specific binding regions, antagonists to the p85 and p110 interaction can be prepared to further study the characteristics and methods to modulate PI3-kinase activity.

The following experiments also show that recombinant PI3-kinase expressed in Sf9 cells exhibit an associated protein kinase activity and that protein-serine kinase activity is intrinsic to the p110 subunit. See Dhand et al., paper entitled "PI3-kinase is a dual specificity enzyme: Autoregulation by an intrinsic protein-serine kinase activity", (hereafter "Dual specificity"), EMBO Journal, Vol.13, No.3, (Feb. 1, 1994), 522–533, the content of which is incorporated herein by reference, in its entirety.

This invention will be better understood by reference to the following examples, which are included here for purposes of exemplification only and are not to be construed as limitations.

EXAMPLE 1

The intersubunit interaction and binding phenomenon between the p85 and p110 subunits of PI3-kinase was studied in order to better understand their relationship and role in PI3-kinase activity.

Through a series of experiments relating to the p110 subunit, it was found that p110 can reconstitute with p85α or p85β to form an active PI3-kinase complex both in vivo and in vitro. It is known that the p85α subunit forms a stable complex with the p110 subunit when they are coexpressed in Sf9 cells, (Hiles, et al., 1992). To determine whether p85β will also reconstitute with p110 protein in an active complex, insect cells were coinfected with either p85α and p110 or p85β and p110 recombinant baculoviruses.

Specifically, insect cells were maintained in culture as described in Summers and Smith 1987 and the p85α and p85β proteins were expressed in insect cells using baculovirus vectors as described previously, (Gout et al., 1992; Otsu et al., 1991). The recombinant baculovirus expressing p110 was described in Hiles et al., 1992.

The association assay was carried out as follows: Sf9 cells were infected with appropriate baculoviruses (as described in Gout et al., 1992; Hiles et al., 1992). Two days post-infection, cells were harvested and lysed in 50 mM Tris HCl, (pH 7.4), 150 mM NaCl, 50 mM NaF, 5 mM EDTA, 1% Triton X-100, 500 μM sodium orthovanadate, 2 mM PMSF, and 100 kallikrein inhibitor units of aprotinin. Lysates were then either immunoprecipitated using appropriate antibodies or were applied to a phosphopeptide affinity column, $DY_{751}VPML(G)$, derived from sequence surrounding tyrosine 751 of human PDGF-β receptor to which PI3-kinase has been shown to bind (Fry et al., 1992; Otsu et al., 1991).

The p110 antiserum was raised as described in Hiles et al., 1992. The affinity purified polyclonal antiserum raised against SDS-PAGE purified p85α was described in Gout et al., 1992. Monoclonal antibodies directed to the p85α and to the p85β proteins are described in End et al., 1993, the content of which is incorporated herein by reference in its entirety. Immunoprecipitation was carried out as described previously in Otsu et al., 1991.

Specifically, Sf9 cells were infected with either p85α, see FIG. 1, Ai (lane 1), p85β (lane 2), or p110 (lane 3) viruses or were coinfected with p85α and p110 viruses (lanes 4–6) or with p85β and p110 viruses (lanes 7–9). Lysates of these cells were precipitated using polyclonal affinity purified antibodies raised against p85α (lanes 1 and 4),1; monoclonal antibodies raised against p85β (lanes 2 and 7); polyclonal affinity purified antibodies raised against p110 (lanes 3, 5, and 8) or bound to immobilized $Y_{751}$ phosphopeptide affinity beads (lanes 6 and 9). Enzyme complexes were analyzed by Coomassie Blue staining 7.5% SDS-PAGE gels or subjected to PI3-kinase assays. PI3-kinase assays were performed on immunoprecipitates as described above, See FIG. 1, Aii.

In double infections of baculoviruses expressing p85α and p110, both proteins were detected in either anti-p85α or anti-p110 immunoprecipitates, or when the enzyme was bound to $Y_{751}$ phosphopeptide affinity beads. See FIG. 1, Ai, lanes 4, 5, 6. It was also found that all affinity and immunoprecipitates possess PI3-kinase activity. See FIG. 1, Aii, lanes 4, 5, 6. The PI3-kinase assay was carried out as described in End et al., 1993.

Similar results were found with viruses expressing p85β and p110. Infected cell lysates immunoprecipitated with antibodies directed to the p85β or the p110 subunit, or if bound to $Y_{751}$ phosphopeptide affinity beads, were found to contain both p85β and p110 when analyzed by SDS-PAGE. See FIG. 1, Ai, lanes 7, 8, 9. These samples were also tested for PI3-kinase activity, which showed that the p85β/p110 complex to be enzymatically active. See FIG. 1, Aii, lanes 7, 8, 9.

The levels of Coomassie Blue staining protein precipitated in the p85β/p110 complex are essentially the same as those seen precipitated in the p85α/p110 complex using identical amounts of both p110 antibody or Y751 phosphopeptide affinity beads. Since both p85α and p85β are expressed to approximately the same levels in insect cells, (Gout et al., 1992), the p85β/p110 complex formation in Sf9 cells is probably as efficient as p85α/p110 complex formation. Because comparable amounts of PI3-kinase activity were precipitated with either the p85α/p110 complex or the p85β/p110 complex, it is probable that p110 is able to form a stable, active PI3-kinase complex with either of the p85 isoforms in insect cells.

EXAMPLE 2

To ascertain whether the two subunits of the PI3-kinase complex are able to associate post-translationally in vitro, a binding assay was carried out.

One subunit of the PI3-kinase complex was first immobilized to an appropriate matrix and then allowed to bind the other subunit in solution.

First, the p85 proteins immunoprecipitated from infected insect cells using isoform-specific monoclonal antibodies were collected on Protein A Sepharose beads. These immunocomplexes were then incubated with lysates of insect cells that had been infected with p110 viruses. They were then washed and subjected to analysis by SDS-PAGE or PI3-kinase assays. Alternatively, p110 was immunoprecipitated from infected insect cell, incubated with p85α expressing lysates, and then treated as described above.

Both p85α and p85β were observed to bind p110 by Coomassie Blue staining following SDS-PAGE, See FIG. 1, Bi, lanes 1 and 2. PI3-kinase activity was also assayed, see FIG. 1, Bii, lanes 1 and 2). Similar results were obtained when p110 was immobilized and the bound p85α protein is detected as Coomassie Blue stained protein on SDS-PAGE following binding in vitro, See FIG. 1, Biii, lane 2.

EXAMPLE 3

In order to determine the specific region of p85α responsible for binding to p110, an analysis of the domains of p85 which are involved in the interaction was undertaken.

Figure 2A:
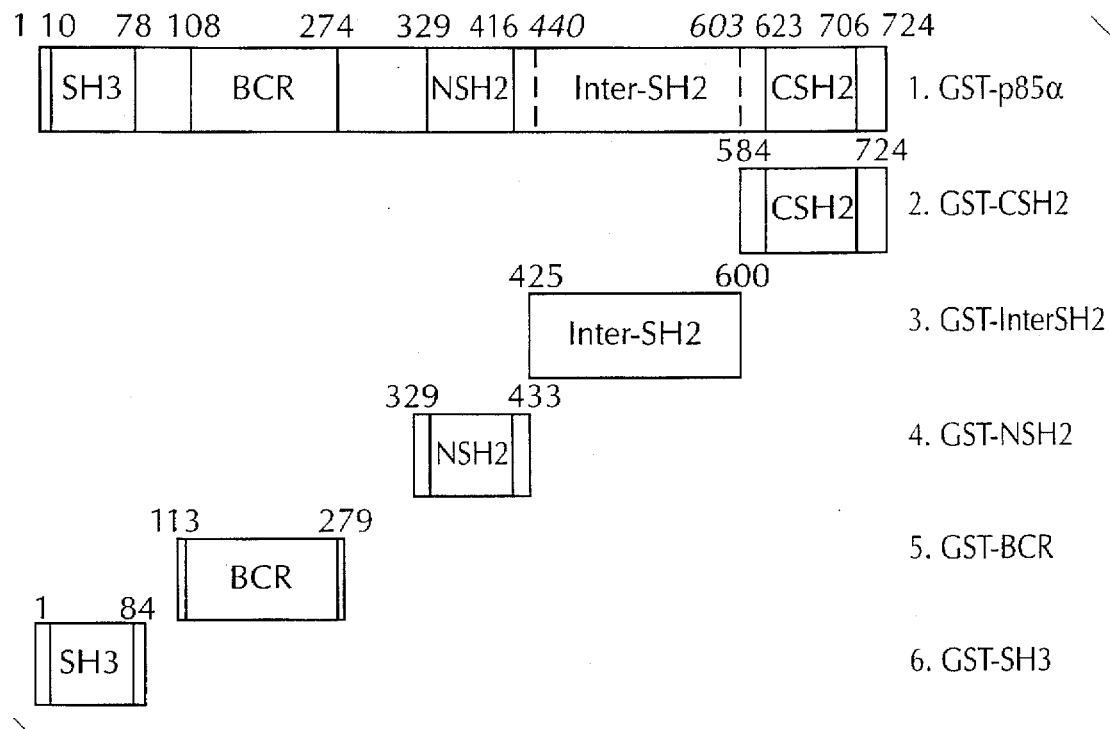
FIG. 2A shows construction of fusion proteins using GST and p85α domains.
Figure 2B:
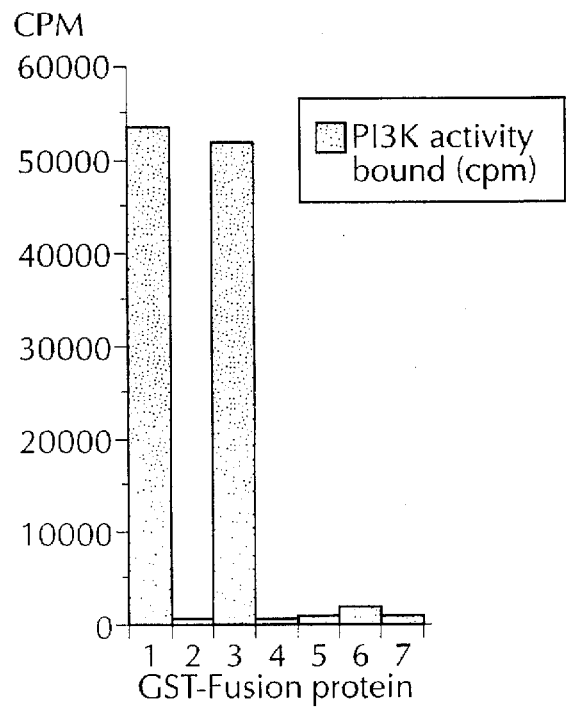
FIG. 2B depicts PI3 kinase activity for these fusion proteins.

GST fusion proteins of the various subdomains of p85α were constructed and immobilized on glutathione-sepharose beads, See FIG. 2, A. These proteins were used for affinity analysis with cell lysates prepared from Sf9 cells infected with a recombinant baculovirus expressing p110. The complexes were washed and subjected to PI3-kinase activity. GST alone, and GST p85α bound to glutathione-sepharose beads incubated with wild-type lysate were used as controls.

FIG. 2, B shows that kinase activity is only associated with either the full length GSTp85α protein (lane 1) or with the inter-SH2 region of the p85α (lane 3). PI3-kinase activity did not bind to GST alone (lane 7) and no endogenous insect cell PI3-kinase activity bound to full length GSTp85α protein when incubated with control lysates (data not shown).

EXAMPLE 4

To study the interaction between the inter-SH2 region of p85α with p110 in the context of the entire p85 protein, monoclonal antibodies which bind to epitopes within the inter-SH2 region were used to block intersubunit associations. p85α from insect cells were immunoprecipitated, either using two monoclonal antibodies, U9 and U15, which bind to epitopes located in the inter-SH2 region of p85α, or with two control antibodies that recognize the BCR domain (End et al., 1993). These immunocomplexes were washed stringently and incubated with lysates of insect cells that had been infected with p110 virus. Bound proteins were then subjected to analysis by SDS-PAGE and PI3-kinase assays.

Figure 3A:
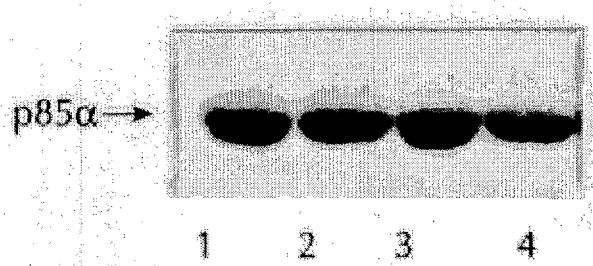
FIG. 3A shows results of immunoprecipitation studies on recombinant p85α produced in Sf9 cells.
Figure 3B:
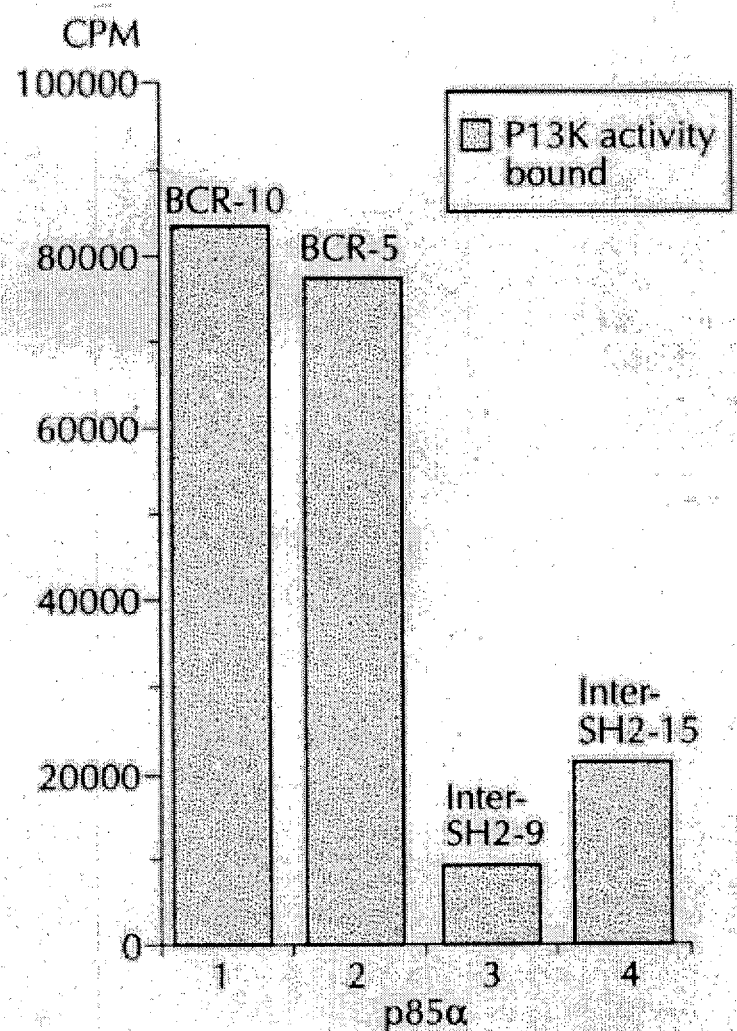
FIG. 3B shows studies using antibodies which bind to the inter-SH2 region and to the BCR domain.

Similar quantities of p85α were found to be immunoprecipitated by all four antibodies as determined by Coomassie Blue stain, see FIG. 3, A, lanes 1–4. However, the amount of PI3-kinase activity that bound to p85α immunoprecipitated with the two antibodies that recognize the inter-SH2 region was significantly less, see FIG. 3, B, lanes 3 and 4, than the activity which bound to p85α immunoprecipitated with antibodies to the BCR domain, see FIG. 3, B, lanes 1 and 2).

From this data, it is apparent that the inter-SH2 region of p85α is required for binding to the p110 subunit, and that antibodies specific to the inter-SH2 region inhibit binding between the subunits.

EXAMPLE 5

Figure 4A:
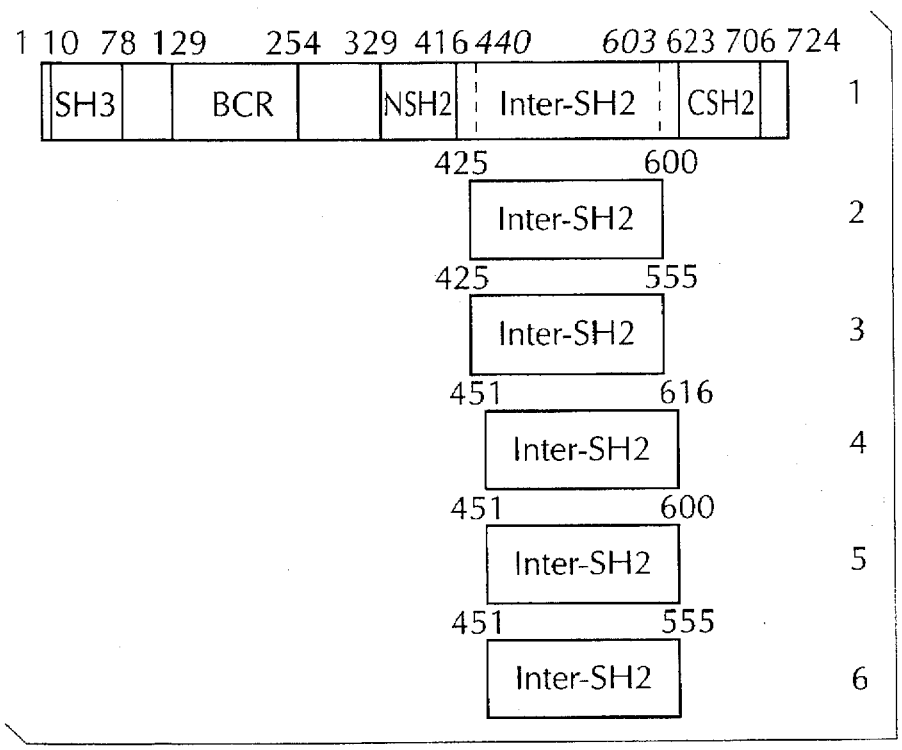
FIG. 4A shows construction of p85α deletion mutants.
Figure 4B:
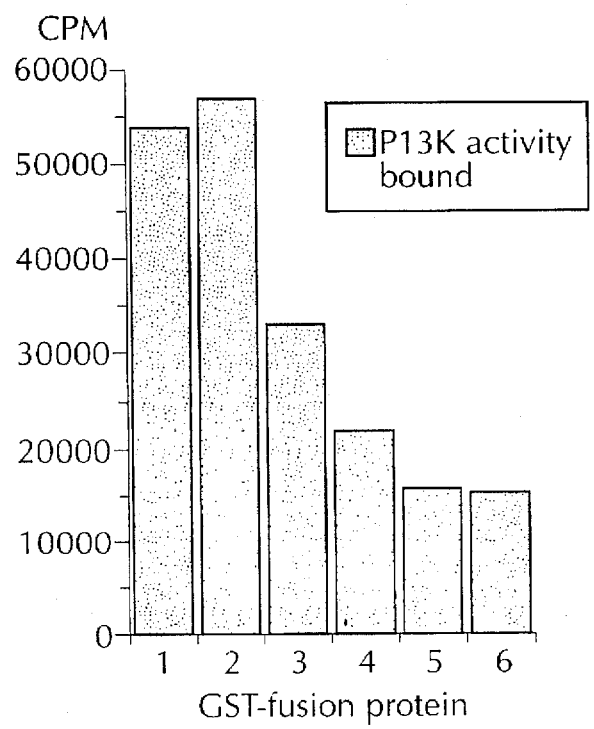
FIG. 4B presents results of PI3 kinase activity assays on the deletion mutants.

In order to define which sub-regions of the inter-SH2 region are involved in directly binding the p110 subunit, deletions were introduced at both ends of the inter-SH2 region of p85α, reducing the size of this region from 175 amino acids (425–600) to 104 residues (451–555), See FIG. 4, A. The truncated inter-SH2 regions, expressed as GST fusion proteins, were bound to glutathione-sepharose beads and then incubated with lysates of insect cells that had been infected with p110. The associated PI3-kinase activity was measured.

Construction of GST-p85α Fusion Proteins

Sequences corresponding to the SH3 domain (amino acids 1–86), the BCR homology region (amino acids 125–322), and the helical inter-SH2 domain (amino acids 425–600, 425–555, 451–616, 451–600, 451–555) of the bovine p85α subunit of the PI3-kinase (Otsu et al., 1991) were amplified by PCR and cloned into the pGEX-2T expression vector (Pharmacia). BamHI and EcoRI sites were included at the N- and C-termini of oligonucleotides respectively to facilitate cloning. Stop codons were introduced at the end of each of the cloned sequences, 5' to the EcoRI site. PCR fragments were verified using the Sequenase system (US Biochemicals). The full length p85α (amino acids 1–724) was subcloned into pGEX-2T by digesting the pGEX-2T-SH3 with BgIII and EcoRI and replacing this fragment with a similarly cut cartridge from p85α in the Blue Script vector (Otsu et al., 1991) which contained the remaining coding region of the p85α protein. The C- and N-terminal SH2 domain of p85α and the p85αN—C construct have been described (Yonezawa et al., 1992).

The results are set forth in FIG. 4, B (lanes 2–6) show that the deletion of amino acids from either end of the inter-SH2 region gradually reduces the amount of bound PI3-kinase activity. Disrupting the inter-SH2 structure probably destabilizes the putative domain and prevents protein-protein interactions. Additionally, the results also identified a structural element of 104 amino acids, between residues 451–555 of the inter-SH2 domain of p85α, that is able to directly bind to the p110 protein and associated PI3-kinase activity, FIG. 4, B, lane 6.

Additionally, a series of nested deletions of GSTp85β fusion proteins from the 3' end of the N-terminal SH2 domain to the 5' end of the C-terminal SH2 domain was constructed to define the binding site within the inter-SH2 region. The interaction of these GST fusion proteins with p110 was then measured as described above.

Construction of GST p85β Fusion Proteins

Full-length p85β, p85β(445–724), p85β(486–724), and p85β(516–724) were described in Yonezawa et al., 1992. See FIG. 5. For p85βΔ486–516, GSTp85β(1–724) was digested with BamHI and BgIII to remove the fragment residues 486–516 and then self-ligated. p85βΔ445–485 and p85βΔ445–469 were constructed by amplifying two PCT products from p85β cDNA (P3 for p85βΔ445–485 and P4 for p85βΔ445–469). P3 encompasses nucleotides 1457–1966 and P4, encompasses nucleotides 1408–1966 and both had an AccI introduced at the 5' end. Both P3 and P4 were digested with AccI and KpnI and then ligated into AccI and KpnI digested GSTp85β1–724 respectively.

Figure 5A:
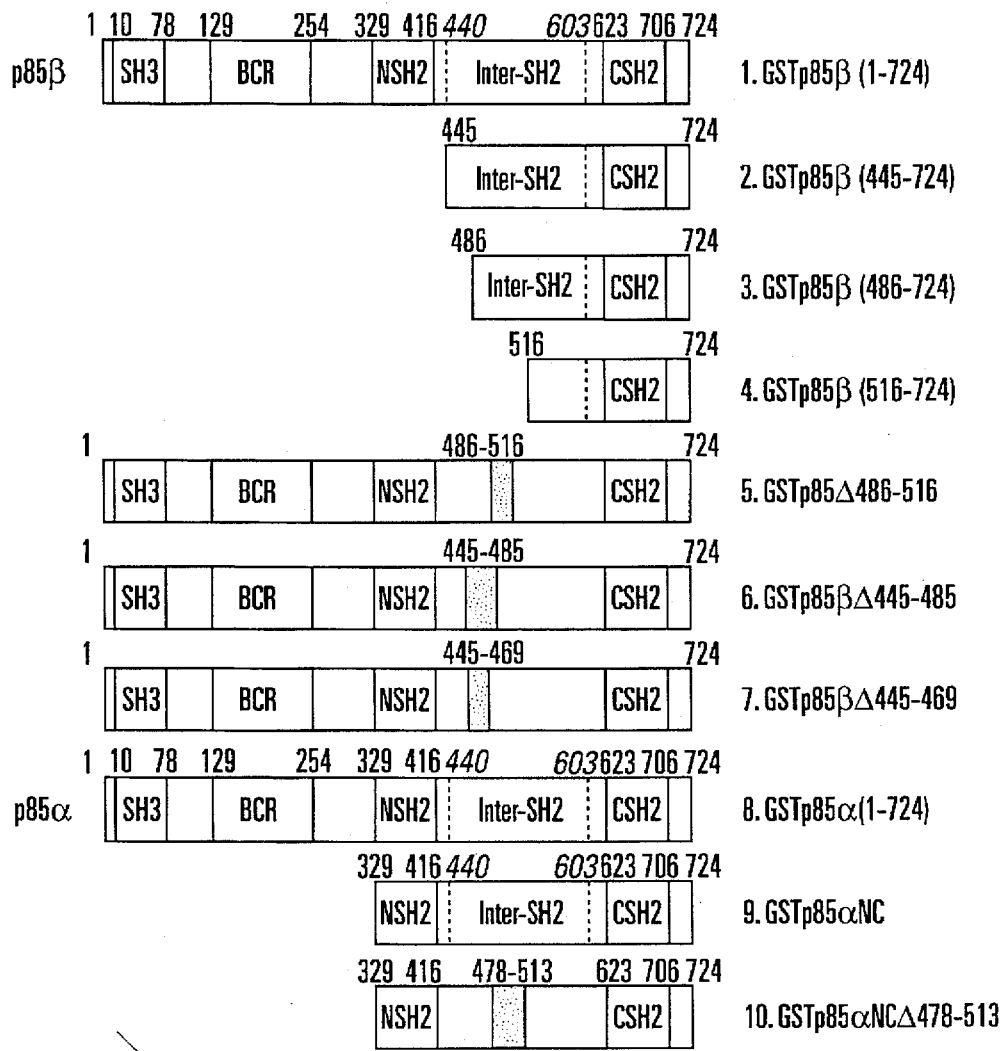
FIG. 5A shows fusion protein constructs of GST-p85β and GST-p85α fusion proteins, using deletion mutants of p85β and p85β.
Figure 5B:
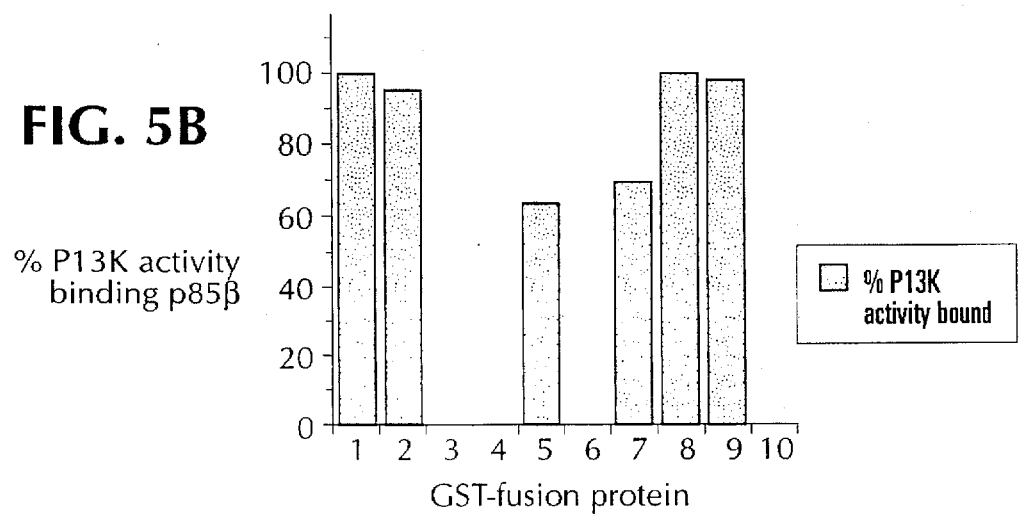
FIG. 5B shows results of a PI3 kinase assay on these fusion proteins.

Full length GSTp85β(1–724) and GSTp85β(445–724), which contains most of the inter SH2 region, were clearly able to bind PI3-kinase activity, see FIG. 5, B, lanes 1 and 2. However, mutants with deletions that advance into the inter-SH2 region as those in GSTp85β(486–724) and in GSTp85β(516–724) were unable to bind PI3-kinase activity, see FIG. 5, B, lanes 3 and 4. These results show that a 71 amino acid region (residues 445–516) in p85β is involved in the interaction between the p85β protein and p110.

In order to more precisely locate the binding site in p85β, mutants that contained deletions in this region, such as GST-85βΔ486–516, GST-85βΔ445–485, and GST-85βΔ445–469, were constructed (see FIG. 5, A, mutants 5, 6, and 7). The function of these mutants was assayed as described above. Following binding, PI3-kinase activity revealed that both GST-85βΔ486–516, and GST-85βΔ445–469, were still able to bind approximately 65% of the PI3-kinase activity, (see FIG. 5, B, lanes 5 and 7), as compared to wild type GSTp85β. However, the deletion mutant GST-85βΔ445–485, (analogous to residues 452–492 in p85α) was unable to bind any detectable PI3-kinase activity, (see FIG. 5, B, lane 6). Thus, it was determined that a 40 amino acid region is absolutely required for binding of PI3-kinase activity to p85β.

To determine whether a similar region of p85α was involved in binding to the p110 protein, an analogous deletion to that made in p85β was constructed, see FIG. 5, A, mutant 10, and assayed for its ability to bind PI3-kinase activity. This deletion mutant, GSTp85αNC2Δ478–513, (analogous to amino acid residues 471–501 in p85β) was unable to bind PI3-kinase activity, see FIG. 5, B, lane 10) in comparison to a similar construct, GSTp85αNC, lacking the deletion, see FIG. 5, B, lane 9). These results define a 35 amino acid region in p85α that is necessary to mediate binding of the p110 catalytic subunit.

Thus, amino acid residues 478–513 of p85α and 445–485 of p85β are absolutely necessary for binding of p110 and PI3-kinase activity.

EXAMPLE 6

Having conducted in vitro analyses on the p85 binding region, the association of PI3-kinase activity with wild-type and mutant p85α in vivo was examined. Full-length p85α and mutant p85α with a deletion within the binding site (p85αΔ478–513) was constructed for transient expression in mouse-L cells.

SRα plasmids (Takebe et al., 1988) for the expression of wild-type bovine p85α (Wp85α) or a mutant bovine full length p85α (p85αΔ478–513) which lack a binding site for p110 were constructed as described (Hara et al., submitted for publication), and designated as SRα-Wp85α(W) and SRαp85αΔ478–513(M), respectively. Semi-confluent mouse L-cells were transfected with 10 μg of either SRα-Wp85α or SRαp85αΔ478–513 plasmids using the DEAE dextran method. Sixty hours later, cells were lysed in a buffer containing 20 mM Tris (pH 7.6), 1% Nonidet P-40, 10% glycerol, 137 mM NaCl, 1 mM MgCl₂, 1 mM CaCl₂, 1 mM DTT, 1 mM PMSF, 1 mM sodium orthovanadate and transiently expressed bovine p85α immunoprecipitated with 2 μg of an anti-p85α monoclonal antibody (G12), which is unable to recognize murine p85α (Yonezawa et al., 1992) bound to protein-G agarose. The samples were then subjected to Western blotting using a polyclonal antibody that recognizes the C-terminal of p85α or PI3-kinase assay.

Figure 6A:
FIG. 6A shows a comparison of immunoprecipitation assays in wild type and mutant p85α, following transfection cells.
Figure 6B:
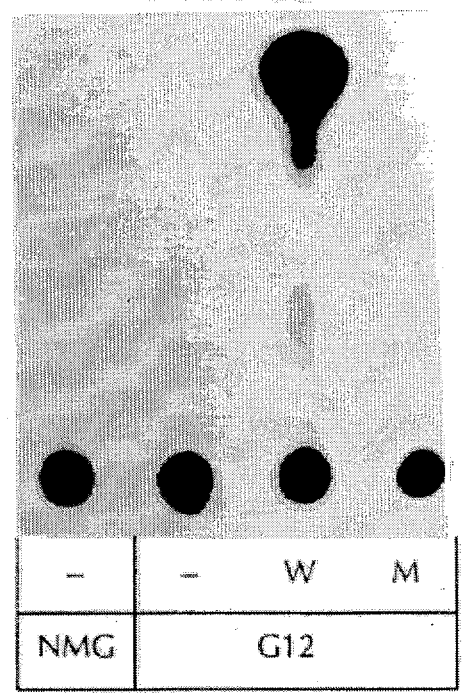
FIG. 6B is results of a PI3 kinase assay on these proteins.

FIG. 6, A, shows that equivalent amounts of wild type (W) and mutant p85α (M) were immunoprecipitated from these cells, see lanes 2 and 3, and no endogenous mouse p85α was immunoprecipitated from untransfected control mouse cells (NMG), lane 1. However, PI3-kinase activity was only found to be associated with the wild-type p85α, see FIG. 6, B, lane 3, and no PI3-kinase activity is observed in immunoprecipitates of mutant p85α, see FIG. 6, B, lane 4, or from untransfected cells, see FIG. 6, B, lane 1.

EXAMPLE 7

After determining the critical regions of p85α and p85β responsible for binding PI3-kinase activity, a study of the comparable region of p110 which interacts with p85α and p85β was undertaken. GST p110 fusion proteins encompassing various regions of p110 were prepared, see FIG. 7, A, and the ability of these p110 fusion proteins to bind p85 expressed in an insect cell expression system was assessed.

Construction of GST-p110 Fusion Proteins

Regions of the p110 cDNA (Hiles et al., 1992) corresponding to amino acids 1–128 (p110-1), 123–458 (p110-2), 577–1068 (p110-3), 601–960 (p110-4), 760–960 (p110-5), 760–1069 (p110-6), 1–49 (p110-1.1), 1–81 (p110-1.2), 1–108 (p110-1.3), 20–81 (p110-1.4) and 20–108 (p110-1.5) were amplified by PCR. BamHI and EcoRI sites were added to 5' and 3' oligonucleotides respectively to facilitate cloning. Following amplification, PCR products were cut with BamHI and EcoRI and ligated into pGEX-2T (Pharmacia). GST fusion constructs expressing amino acids 1–35 (p110-1.6) and 37–128 (p110-1.7) were constructed from as follows. For plasmid p110-1.6, p110-1 was digested with BsmI and EcoRI, the ends were made blunt by treatment with T4 DNA polymerase and the plasmid was circularized with T4 DNA ligase. For plasmid p110-1.7, p110-1 was digested with BsmI and the ends were made blunt with T4 DNA polymerase. BglII linkers (12-mers: New England Biolabs) were added to the ends and the plasmid further restricted with BamHI. The plasmid containing band was gel-purified and the plasmid recircularized with T4 DNA ligase. Expression constructs were transformed with *E. coli* XL1-blue (Stratagene). Expression of glutathione S-transferase (GST) fusion proteins was carried out as described previously (Smith and Johnson, 1988).

Figure 7A:
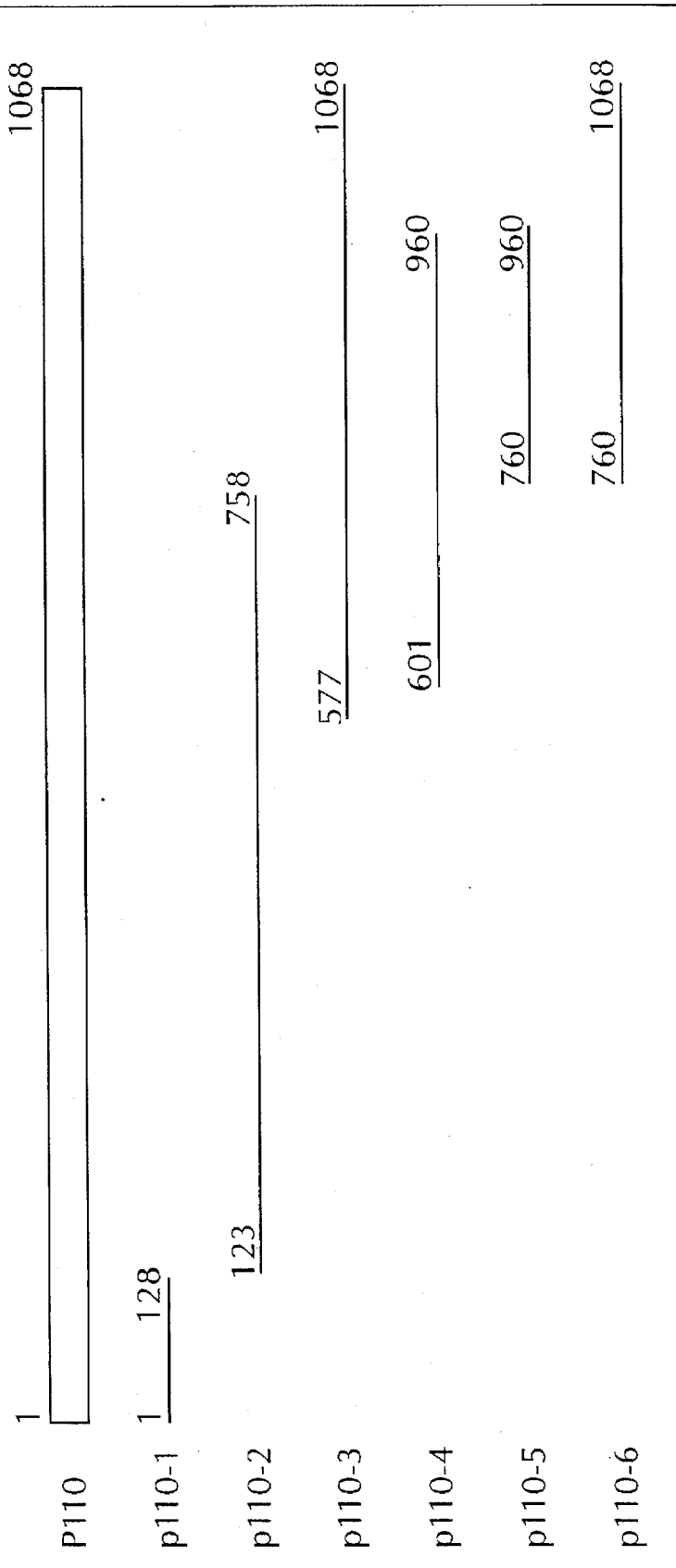
FIG. 7A shows construction of various GST-p110 fusion proteins.

FIG. 7, B, shows that of the six fusion proteins, p110.1–p110.6, only p110.1 was able to bind to p85α (lane 16) and p85β (lane 17) with high affinity. No binding was detected in the control Sf9 cell lysate and no binding to either subunit was seen in experiment made with any other constructs. This indicates that the region comprising amino acid residues 1–128 of p110 contains a binding site for the p85 proteins.

Figure 8B:
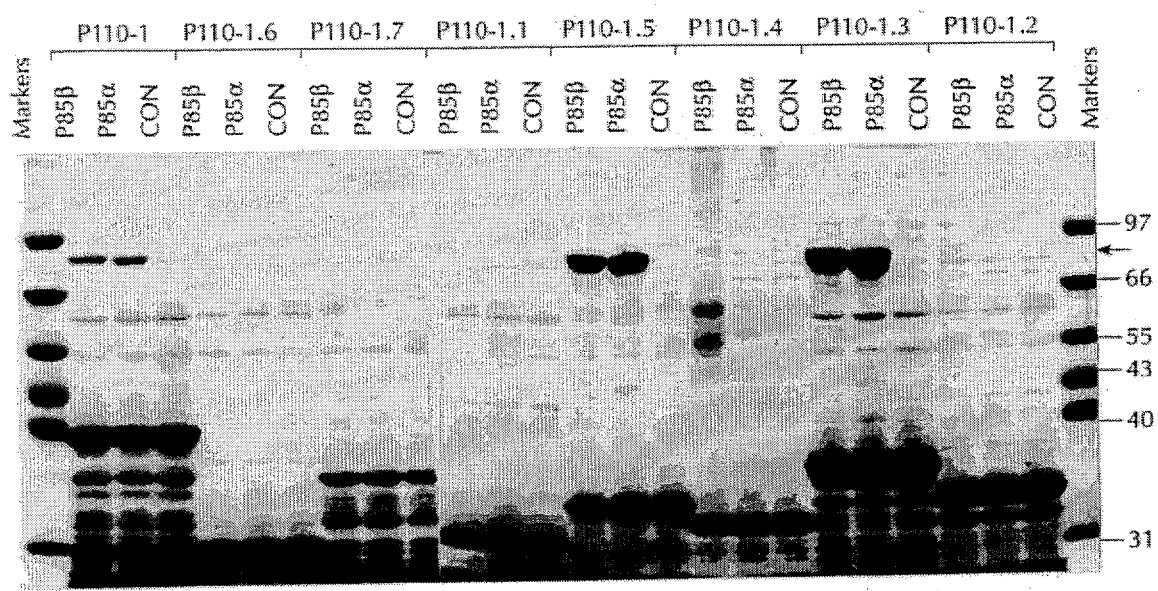
Figure 10A:
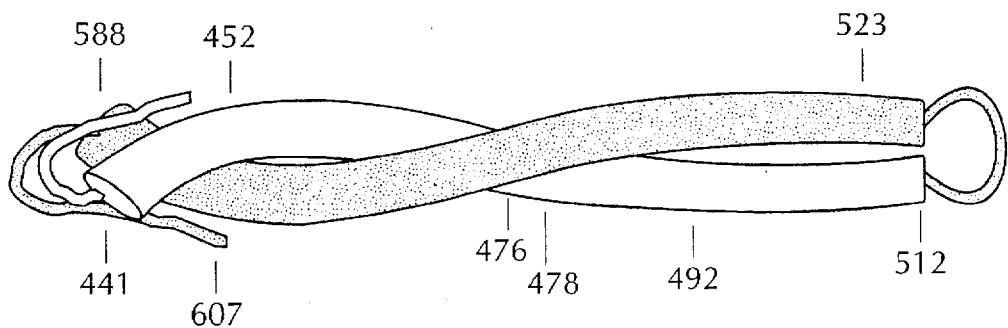
FIGS. 10A, B, C and D, inclusive, depict the coiled-coil domain of p85α.
Figure 10B:
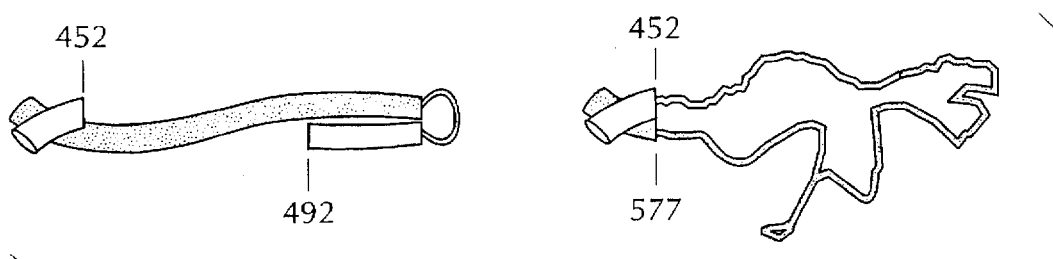
Figure 10C:
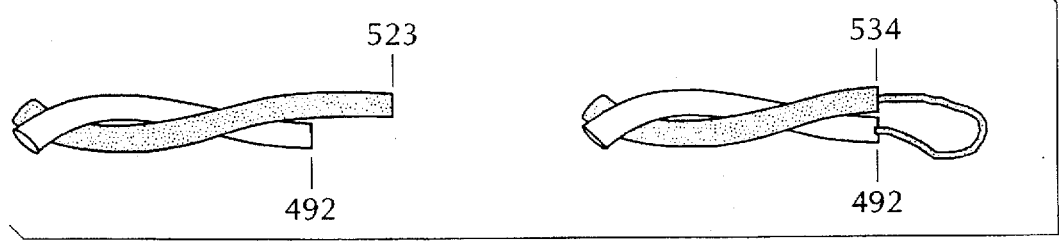
Figure 10D:
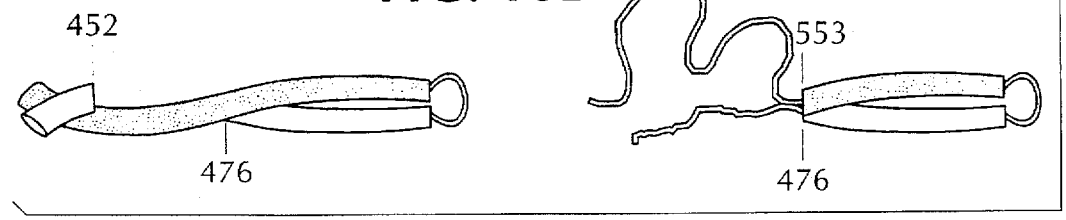
Figure 12A:
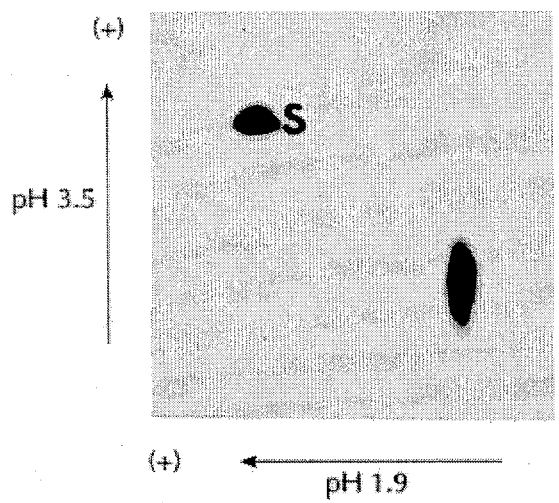
FIG. 12A is a study of phosphorylation of p85 subunits, following affinity purification.
Figure 12B:
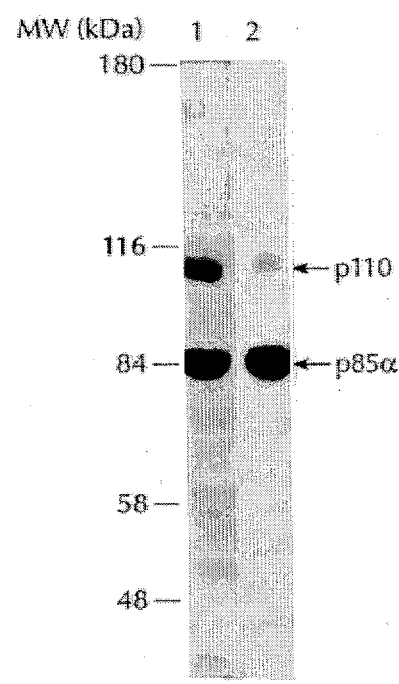
FIG. 12B compares phosphorylation of p85α and p110, via Coomassie Blue staining.
Figure 12C:
FIG. 12Ci depicts a phosphoamino acid analysis of p85α.
Figure 12D:
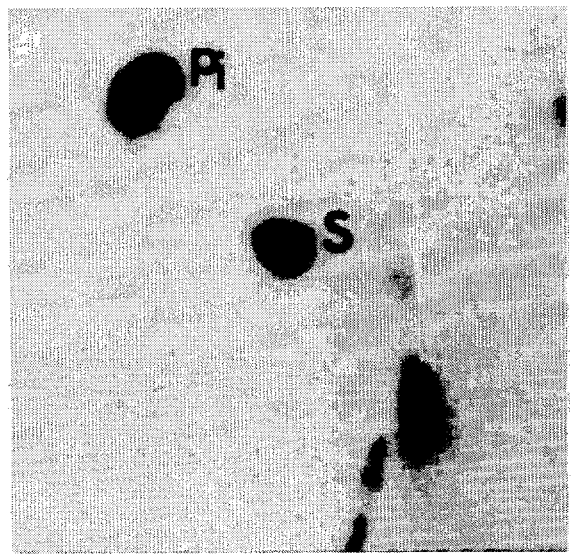

Seven other GST fusion proteins, p110-1.1–p110-1.7, were constructed which encompassed the various regions of the first 128 amino acids of p110, see FIG. 8, A). Of these, p110-1.3 and p110-1.5, bound both p85α and p85β, see FIG. 8, B, lanes 20, 21 and 14, 15 respectively. None of the other constructs showed any ability to bind either p85 subunit. These results indicate that amino acid residues 20–108 of the p110 is the minimum structural element which is required for binding the p85 subunit.

EXAMPLE 8

Based on the binding region of the p85 and p110 subunits, the structure of the inter-SH2 region was further investigated.

It has been suggested that the inter-SH2 region is largely α-helical in character and that a four helix bundle might be present, Panayotou et al., 1992. The sequence of the inter-SH2 region was used to search the amino acid sequences in the Owl 19.0 database (Protein Engineering Club, Leeds University, U.K.); twelve of the top 20 matches were with sequences from proteins myosin or paramyosin sequences which have coiled-coil regions. The top five matches found were with isoforms of p85. Although the percentage sequence identity between the aligned amino acid sequences was relatively low, heptad repeats were often aligned.

The amino acid sequences of proteins in the Brookhaven databank of protein structures (Bernstein et al., 1977) was also searched. Two of the top three sequences found to be similar were with tropomyosin, a two stranded α-helical coiled-coil muscle protein which structure has been solved to 15 angstrom resolution (Philips et al., 1979). Similarly, although the amino acid sequence identity with tropomyosin was quite low (20% over 175 amino acid residues), the heptad repeats in the inter-SH2 region and that of tropomyosin were in register for a considerable part of the alignment. Sequence analysis of tropomyosin (Hodges et al., 1972; Parry, 1975; McLachlan and Stewart, 1975) showed an unbroken series of heptad repeats (a,b,c,d,e,g)n, where residues a and d are conserved as hydrophobic residues, which suggested that the structure would be a coiled-coil of α-helices. Earlier sequence analysis data of the helical domain of p85α and p85β , (Panayotou et al., 1992, the contents of which is incorporated herein in its entirety), showed the presence of two long unbroken heptad repeats of the form (a,b,c,d,e,f,g)n where the a and d are hydrophobic.

The heptad repeats in the inter-SH2 region of p85 and the similarity of its amino acid sequence with sequences of coiled-coil proteins, such as tropomyosin, paramyosin, and myosin suggest that the domain might consist of a coiled-coil of α-helices. Further analysis of the inter-SH2 region showed that its sequence is consistent with the structure being an anti-parallel coiled-coil of two seventy-residue α-helices (residues 441–512 and 518–588 in p85α), See FIGS. 9 and 10.

When deletions in the p85α protein and those in the p85β protein are compared and considered with the corresponding loss of activity, the third quarter of helix-1 of the coiled-coil, residues 478–492 in p85α, was identified as the common region between the two p85 proteins that is absent in deletion mutants that are unable to bind PI3-kinase activity, see FIG. 10, A. Deletions which remove either the top half of helix 1, residues 452–476 on p85α (see FIG. 10, D) or the lower quarter of helix-1, residues 492–523 on p85α (see FIG. 10, C) destabilize the coiled structure and disrupt the association with the p110 protein, but does not completely inhibit its binding. Only when residues 478–492 of p85α are removed, is a complete loss of function observed (see FIG. 10, B) and the p110 protein is seen not to bind p85.

Figures 9B, 9D:
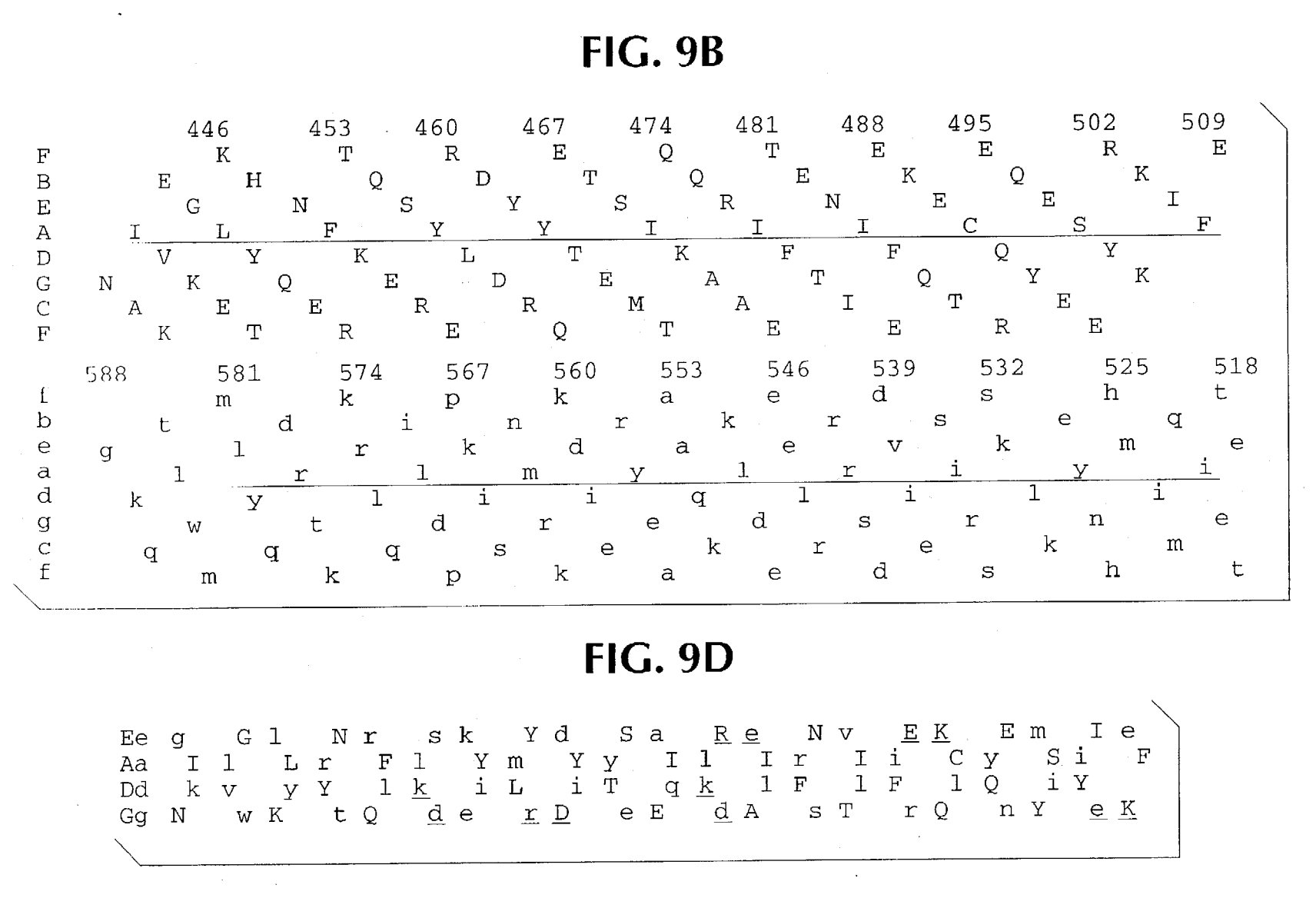

Sequence analysis of both the p85 proteins reveals that residues 478–492 of p85α are contained in three heptad repeats (residues 470–497 in p85α) which are identical between the two proteins at the amino acid level except for a single conservative amino acid change (see FIG. 9, A). A synthesized peptide of residues 470–497 of p85α was chemically coupled to Sepharose beads but was unable to bind to p110 and PI3-kinase activity. Analysis of p110 binding characteristics of p85 deletion mutants suggest that while helix-1 of the inter-SH2 region is primarily responsible for the interaction between the two subunits of the PI3-kinase complex, helix 2 likely donates a structural element to the folding of helix-1. In order to produce a stable structure, regions corresponding to 470–497 on helix-1 of p85α and the adjacent region on helix-2 are probably required for the interaction between the p85 and p110 subunits to take place.

At positions a and d of the heptad repeat, 75.6% of the residues are apolar. Forty-nine percent of the amino acids at the external positions of the helices (b,c,e,f,g) are charges whereas only 12% of residues at positions a and d are charged. The relatively high proportions of Ile, Phe, and Tyr at positions a and d compared to other coiled-coil proteins (Conway and Parry, 1990) might be related to the likelihood that the p85 helices are anti-parallel, whereas in other coiled coil proteins helices are parallel.

The binding between the p85 and p110 proteins is of very high affinity and no suitable conditions have been established which result in dissociation of an active PI3-kinase complex (Fry et al., 1992, Ruiz et al., 1993). In addition, it is known that the interaction between the two subunits is not dependent on the presence of phosphotyrosine (R. Dhand, unpublished), and there are no proline-rich motifs in the region of p110 which may provide a binding consensus for the p85 protein. Secondary structure prediction using the Leeds Prediction Package (Eliopoulos, 1989) predicts that about 60% of the N-terminal 120 residues, that have been shown to directly bind the p110 proteins, will adopt an α-helical conformation and some 20% a β sheet conformation. Thus, the N-terminal region of p110 will consist of a α/β region, wherein the α-helices might form interactions with the inter-SH2 region of p85. Since the major binding site on p85α is considered to be between residues 478–492 on Helix-1, it is of interest that there is a small hydrophobic pocket in this region formed by Met-479 (C position on FIG. 9, C, Ala-483 (G position on FIG. 9, C, and Ala-496, (C position in FIG. 9, C). As the N-terminus of p110 is approximately 48% hydrophobic in character, this pocket may be important in forming a high affinity interaction with the p110 protein.

A lipid-binding site has also been identified in the inter-SH2 region of the p85 protein. Two monoclonal antibodies that specifically recognize this region have been shown to inhibit the binding of phospholipids, in particular PI 4,5P$_2$ to the p85 subunit (End et al., 1993). Amino acid sequence analysis reveals the presence of a short basic motif in the inter-SH2 region of the p85α protein, similar to that found in profillin and gelsolin and demonstrated to confer PI 4,5P$_2$ binding properties to these proteins (Jamey et al., 1992; Yu et al., 1992). Moreover, analogous residues are well conserved in p85β, which suggests that it plays a regulatory site for these proteins. As the p85 protein has been shown to bind to p110 via the inter-SH2 region, the lipid binding site probably form a part of the substrate binding pocket for PI3-kinase, specific for PI 4,5P$_2$.

EXAMPLE 9

In addition to the study of intersubunit interactions of the PI3-kinase, a protein serine/threonine kinase activity has been reported in immunoprecipitates of rat liver PI3-kinase, Carpenter et al., 1993. However, this study does not disclose whether this activity represents a tightly bound cellular enzyme, or is intrinsic to a component of the PI3-kinase complex. In fact, Carpenter implies that the serine kinase activity is physically associated with PI3-kinase but is distinguishable from PI3-kinase. The process of cDNA cloning and subsequent expression of the two subunits of the enzyme has allowed a more detailed investigation of the associated serine kinase. These studies are elaborated as follows:

Insect cells (Sf9) were infected with baculoviruses which mediate expression of either p85α or p85β alone, or were coinfected with a virus which expressed p110. The p85α/p110 and the p85β/p110 complexes were either immunoprecipitated with antibodies directed to the p85 or the p110 subunit, or the complexes were bound to a Y$_{751}$ phosphopeptide affinity column (Otsu et al., 1991; Fry et al., 1992). The bound proteins were then used in protein kinase assays.

Specifically SF9 cells were infected with wild type virus (FIG. 11, lanes 1–4); p85α (lane 5); p85β (lane 6); or were coinfected with p85α/p110 viruses (lanes 7, 8, and 9) or with p85β/p110 viruses (lanes 10, 11, and 12). Lysates of these cells were precipitated using polyclonal, affinity purified antibodies raised against p85α (lanes 1 and 7); monoclonal antibodies raised against p85β (lanes 2 and 10); polyclonal, affinity purified antibodies raised against p110 (lanes 3, 8, and 11) or bound to an immobilized $Y_{751}$ phosphopeptide (lanes 4, 5, 6, 9, and 12). Samples were subjected to in vitro protein kinase assays and analyzed by SDS-PAGE and autoradiography.

The results show that in the absence of p110, neither p85α nor p85β could be phosphorylated in vitro, see FIG. 11, (lanes 5 and 6). However, when the insect cells were coinfected with viruses expressing p110, both the p85α and the p85β proteins were found to be heavily phosphorylated when analyzed following immunoprecipitation using antibodies directed to either subunit of the complex, see FIG. 11, lanes 7–8 and 10–11, or after binding to the phosphopeptide column, see FIG. 11, lanes 9 and 12. The p110 protein was not phosphorylated significantly under these conditions and no other phosphorylated proteins were detected in precipitations with either antibodies or with the phosphopeptide affinity beads from control infected cells, see FIG. 11, lanes 1–4.

In addition, lysates of insect cells coinfected with p85α/p110 viruses were immunoprecipitated using anti-p85 polyclonal antibodies. Samples were then subjected to protein kinase assays in the presence of varying amounts of $Mn^{2+}$ and $Mg^{2+}$ and analyzed by SDS-PAGE and autoradiography (data not shown). Results of these experiments comparing the effect of the presence of $Mn^{2+}$ and $Mg^{2+}$ on kinase activity showed that, in fact, this kinase activity was completely dependent on the presence of $Mn^{2+}$. This agrees with the metal ion requirement of the serine kinase activity which was found associated with PI3-kinase purified from rat liver, Carpenter et al., 1993.

EXAMPLE 10

Phosphoamino acid analysis of the PI3-kinase complex, which was affinity purified using $Y_{751}$ phosphopeptide, was also carried out to determine the nature of the protein kinase activity associated with the complex. After affinity purification, phosphorylation in vitro revealed that the p85 subunit contained exclusively phosphoserine, see FIG. 12, A, in agreement with Carpenter et al., 1993. The level of phosphate incorporated in the p110 subunit in vitro under identical conditions was too low to allow phosphoamino acid analysis.

To examine the phosphorylation state of the PI3-kinase complex in vivo, insect cells were coinfected with p85α and p110 expressing baculoviruses and metabolically labelled with $^{32}P$—$PO_4$. Lysates of these cells were bound to $Y_{751}$ phosphopeptide beads which were then washed and SDS buffer eluted proteins visualized by Coomassie Blue staining after SDS-PAGE gel analysis. Autoradiography of these gels revealed a much higher level of phosphate incorporated into p85α than into p110 with respect to the amount of protein present determined by Coomassie Blue staining, (see FIG. 12, B, lanes 1 and 2). Phosphoamino acid analysis revealed that the p85α contained both phosphoserine and phosphothreonine when labelling was carried out in vivo (see FIG. 12, Ci), while the p110 subunit contained only phosphoserine (see FIG. 12, Cii).

Anti-p110 immunoprecipitates of p85α/p110 were used to study the kinetics of phosphorylation. The Km (ATP) for the phosphorylation of p85α was measured as approximately 4 μM. The stoichiometry of phosphorylation of p85α was then measured in the presence of excess ATP (50 μM). Approximately 0.9 mol of phosphate was incorporated into one mol of p85α protein. This extent of phosphorylation is in agreement with that observed for PIK kinase reported to be associated with the PI3-kinase purified from rat liver, Carpenter et al., 1993, and this suggests that a single major autophosphorylation site is being used.

EXAMPLE 11

It is clear now that the protein serine kinase activity of PI3-kinase is intrinsic to the p110 subunit and is not due to an associated insect cell kinase activity.

By mutating the p110 subunit, it was found that both PI3-kinase and protein serine kinase activities were abolished. Because neither of the p85 protein amino acid sequences exhibit any recognizable motifs to those found in other protein kinases, Hanks et al., 1988, or to those of ATP or GTP-binding domains in other proteins, (Saraste et al., 1990), the p110 subunit, which does have redundant kinase motifs and can transfer phosphate from ATP to PI, is the most likely candidate to possess an intrinsic protein-serine kinase activity. The p110 subunit contains amino acids which are conserved in the active sites of known protein kinases and the yeast PI3-kinase, Vps34p, Hiles et al., 1992. The DRHNSN sequence is essential for binding the nucleotide phosphate moieties and for phosphotransferase activity in classical protein kinases, Taylor et al., 1992.

The functional significance of the DRHNSN (SEQ ID NO: 3) sequence which is clearly shared between the phosphoinositide kinase and known protein kinases was studied utilizing site-directed oligonucleotide mutagenesis. A point mutation which converts arginine 916 to proline (R916P) within the DRHNSN motif of bovine p110 was carried out, the protocol of which is set forth in detail in Dhand et al., Dual Specificity.

Briefly, the arginine 916 of p110 was changed to a proline residue by oligonucleotide mediated site-directed mutagenesis. The oligonucleotide 5'TGGGAATTGGGGATCCTCACAATAGTA-3' (SEQ ID NO: 4) was synthesized (Genosys Biotechnologies Inc., Cambridge U.K.) and used to incorporate the R916P mutation into p110-Bam HI (Hiles et al., 1992) using the Stratagene "Double Take" mutagenesis kit. In addition to the R916P mutation, this oligonucleotide also introduces a novel BamHI site by means of silent codon changes. The sequence of a 802 base pair PstI-HindIII cartridge containing the R916P mutation was verified by DNA sequence analysis.

For expression in Sf9 cells, a 903 base pair PstI-KpnI cartridge from the baculovirus transfer vector, p36C-P110 (Hiles et al., 1992) was replaced with the corresponding cartridge from the p110 BamHI plasmid containing the R916P mutation.

Experiments involving mutagenesis identified the p110 subunit as the catalytic subunit of the PI3-kinase. See FIG. 13, A: Coomassie Blue stain of a 7.5% SDS-PAGE of lysates of infected insect cells immunoprecipitated with the described antibody and treated as follows: anti-p85α (lane 1); anti-p110 (lane 2); anti-p85α immunoprecipitate, incubated with p110 containing Sf9 cell lysate in vitro (lane 3); anti-p110 immunoprecipitate of insect cells coinfected with p85α/p110 viruses (lane 4); anti-p85α (lane 5); anti-p110 immunoprecipitate of insect cells infected with p110-R916P (lane 6); anti-p85α immunoprecipitate incubated with mutant p110-R916P containing Sf9 cells in vitro (lane 7); anti-p110 immunoprecipitate of insect cells that had been coinfected with p85α/mutant p110-R916P viruses (lane 8); and B: PI3-kinase assays were performed on immunoprecipitates infected and described in A above.

The effects of the mutation on the intrinsic phosphoinositide kinase activity were first assessed. Insect cells were infected with p85α and p110 viruses either separately or together. Immunoprecipitated p85α and p110 could then be visualized as Coomassie Blue stained proteins following resolution on SDS-PAGE gels, see FIG. 13, A, lanes 1 and 2.

The protein was found to form a stable complex with p85α, if the two proteins were allowed to associate in vitro, or alternatively, if they were coexpressed in insect cells, as can be seen in the SDS-PAGE analysis, see FIG. 13, A, lanes 3 and 4. PI3-kinase assays of these samples showed that the p110 protein alone was active, see FIG. 13, B, lane 2. An active complex was formed when p110 was bound to p85α either in vitro or in vivo, see FIG. 13, B, lanes 3 and 4. Immunoprecipitated p110-R916P was also visualized by Coomassie Blue staining of SDS-PAGE gels, see FIG. 13, A, lane 6, and was seen to comigrate with wild type p110 protein, see FIG. 13, A, lane 2.

A stable complex was recovered when insect cells coinfected with mutant p110-R916P and p85α were analyzed by immunoprecipitation using anti-p110 antibodies, see FIG. 13, A, lane 8, or when mutant immunopurified p110-R916P was allowed to associate with p85α in vitro, see FIG. 13, A, lane 7.

The immunoprecipitates, which contained the mutant p110, were all found to lack PI3-kinase activity, see FIG. 13, B, lanes 6, 7, 8. As the expression and binding capabilities of the mutant p110-R916P were commensurate with those of the wild type p110, this data shows that the mutation has likely disrupted the catalytic site of the protein without completely disrupting the structure of the p110 protein.

EXAMPLE 12

The PI3-kinase inactive mutant p110-R916P was used to study the effect of the mutation on the associated protein serine kinase activity. See FIG. 14. Insect cells were coinfected with p85α and wild type p110 (lane 1); p85α and mutant p110-R915P viruses (lane 2); p110 alone (lane 3); mutant p110-R916P alone (lane 4). Lysates of these cells were immunoprecipitated with antibodies directed against the p110 subunit and the immunoprecipitated proteins were then phosphorylated in vitro.

The p85α subunit was seen to be phosphorylated in vitro when in complex with wild type p110, see FIG. 14, A, lane 1. However, in contrast, the p85 subunit associated with the mutant p110-R916P was not phosphorylated in this assay, see FIG. 14, A, lane 2. Neither the wild type p110 nor the mutant p110-R916P alone was observed to autophosphorylate see FIG. 14, A, lanes 3 and 4.

EXAMPLE 13

The possibility that the p110 subunit could exhibit a trans-kinase activity by binding to, and phosphorylating p85α in vitro was examined. The results of the following experiment is set forth in FIG. 14, B. p85α from insect cells were affinity purified from Sf9 cells using a $Y_{751}$ phosphopeptide column and then incubated with lysates of Sf9 cells infected with baculovirus recombinants expressing p110 (lane 1); mutant p110-R916P (lane 2); untreated (lane 3). The complexes were washed, subjected to in vitro protein kinase assays, then analyzed to SDS-PAGE and autoradiography.

The p85α protein expressed alone was not phosphorylated, see FIG. 14, B, lane 3, while the p85α that was bound in vitro to wild type p110 was heavily phosphorylated, see FIG. 14, B, lane 1. In contrast, p85α complexed with mutant p110-R916P was not phosphorylated, see FIG. 14, B, lane 2.

To ensure that the phosphorylation of p85α is not exclusively associated with p85 expressed in the insect cell system, bacterially expressed p85α as a GST fusion protein was employed as an alternative source of the protein. GST-p85α was bound to affinity resin and then treated as set forth in the preceding paragraph. Following binding, in vitro kinase assays revealed that the GST p85α alone had no associated protein kinase activity, see FIG. 14, C, lane 3, but upon association with wild type p110, the p85α fusion protein became heavily phosphorylated, see FIG. 14, C, lane 1. There is no phosphorylation of GSTp85α bound to the mutant p110-R916P detected, see FIG. 14, C, lane 2.

EXAMPLE 14

Figure 15:
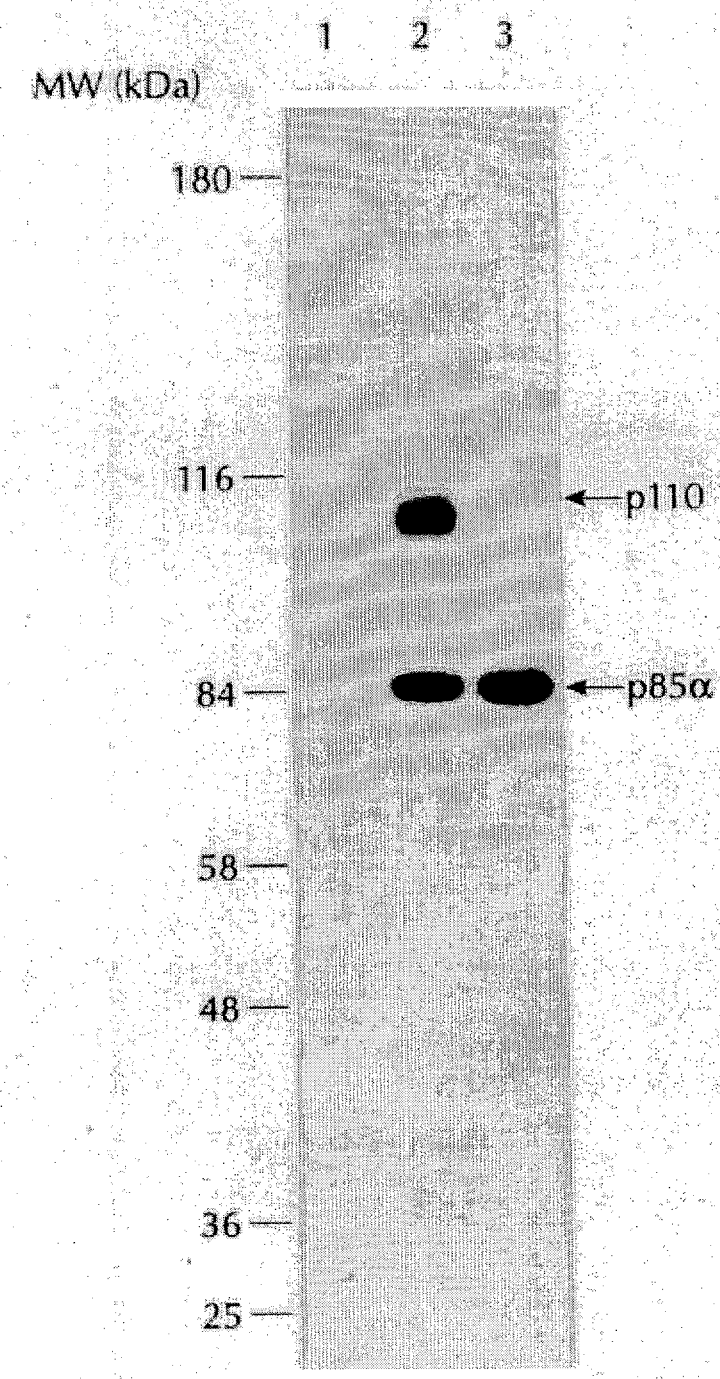
FIG. 15 is an SDS gel of experiments designed to see if p85α complexes to other proteins.
Figure 16A:
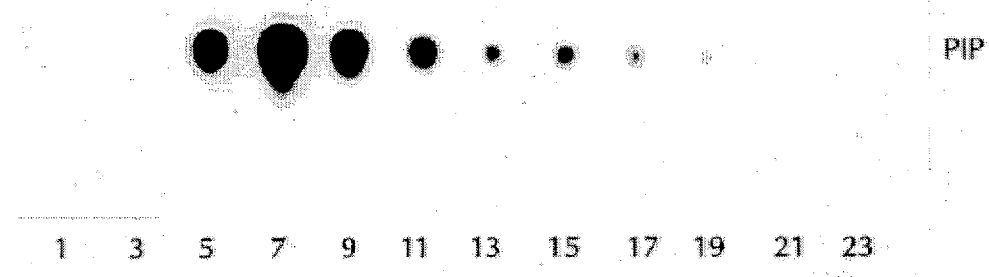
FIG. 16A shows sucrose gradient analysis of Sf9 fractionates of cells wherein express recombinant p110.
Figure 16B:
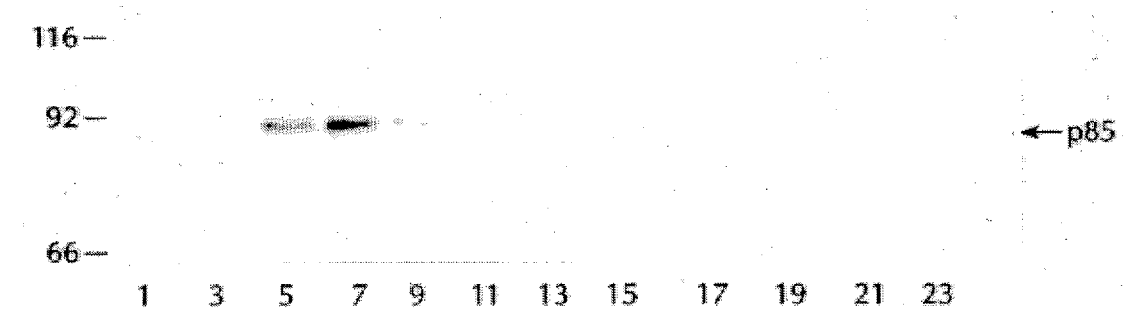
FIG. 16B is a kinase activity assay following incubation of the immunoprecipitates of 16A with pure p85α.
Figure 16C:
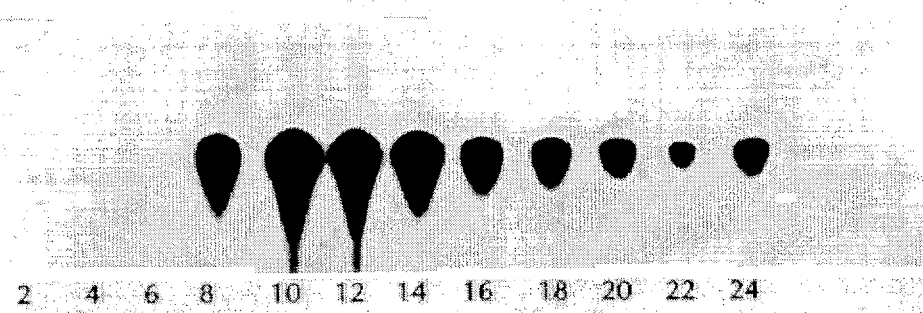
FIG. 16C is a sucrose gradient analysis of lysates of cells, cotransfected to product p110 and p85α.
Figure 16D:
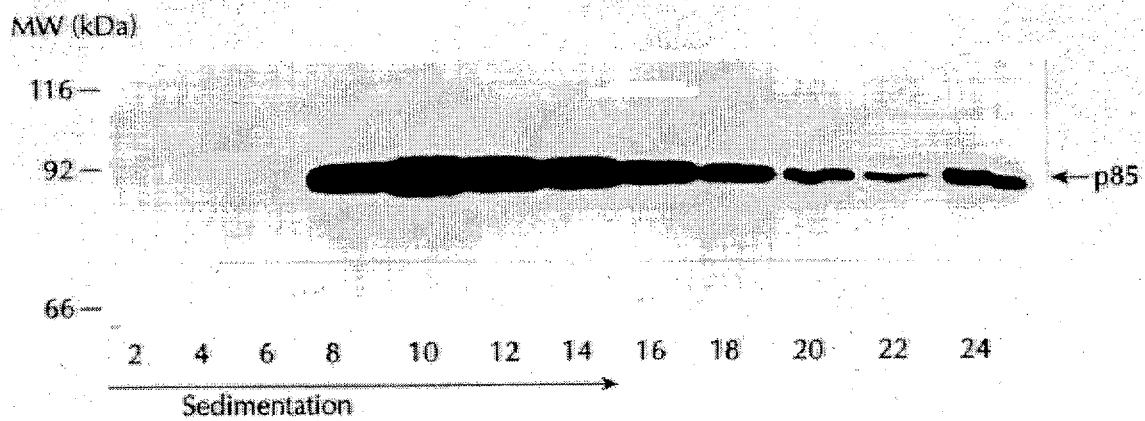
FIG. 16D is a kinase activity assay on the precipitated of 16C.

Further experiments were conducted in order to determine whether other proteins are detected in association with p85 and p110. The results are set forth in FIG. 15.

Specifically, insect cells infected with wild type virus (lane 1); p85α and p110 viruses (lane 2); or p85α alone (lane 3), were labelled with $^{35}S$ methionine for 16 hours. Lysates of these cells were then bound to a $Y_{751}$ phosphopeptide column. After several washes, radiolabelled proteins released by SDS buffer were analyzed by SDS-PAGE and detected by autoradiography.

The results do not reveal any proteins bound to the affinity phosphopeptide from insect cells infected with wild type baculovirus. Furthermore, from cells that had been infected with either recombinant baculovirus expressing p85α alone, or p85α together with p110, no other associated proteins were detected even after a three day autoradiographic analysis.

Sucrose gradient analysis was also conducted to fractionate and purify macromolecules. The results are set forth in FIG. 16. Lysates of Sf9 cells infected with either p110 virus alone, or with p110 and p85 viruses together, were separated on sucrose gradients, and the fractions were assayed for PI3-kinase and protein-serine kinase activity. Sedimentation was from left to right. PI3-kinase activity was immunopurified from fractionated cell lysate expressing p110 (FIG. 16, A) and p110/p85α (FIG. 16, C). The analysis of p110 infected cells separated on a sucrose gradient revealed the bulk of PI3-kinase activity (FIG. 16, A) and p110 protein (data not shown) sedimented with a molecular weight comparable with its migration as a monomer, with a peak in fraction 7.

As p110 does not autophosphorylate significantly as demonstrated above, and thus cannot be detected, p85 was used as an exogenous substrate for protein kinase activity. Immunoprecipitates of each fraction were made and incubated with purified p85α protein, Gout et al., 1992, and then assayed for kinase activity. Results in FIG. 16, B shows a peak of phosphorylated p85, which comigrated precisely with the peak of PI3-kinase activity.

A similar analysis was performed on lysates of insect cells that had been coinfected with p110 and p85α viruses. The PI3-kinase activity sedimented with a molecular weight consistent with that of a heterodimer of p110 and p85α, peaking in fractions 10–12 (FIG. 16, C). The protein-serine kinase activity that had been immunoprecipitated with antibodies specific for either p110 (FIG. 16, D) or p85 (data not shown) also comigrated with PI3-kinase and the bulk of p85 and p110 proteins. This data shows that protein-serine kinase activity is likely to be intrinsic to the PI3-kinase complex.

EXAMPLE 15

It has also been determined that both kinase activities have a similar thiol requirement. PI kinases isolated from a number of eukaryotic sources are known to be sensitive to treatment with sulphydryl-modifying reagents (Hou et al., 1988; Scholz et al., 1991), as well as in other kinases (Muirhead et al., 1986)

To determine whether PI3-kinase and the associated serine kinase activities have a similar thiol requirement, the following experiments were carried out.

Figure 17A:
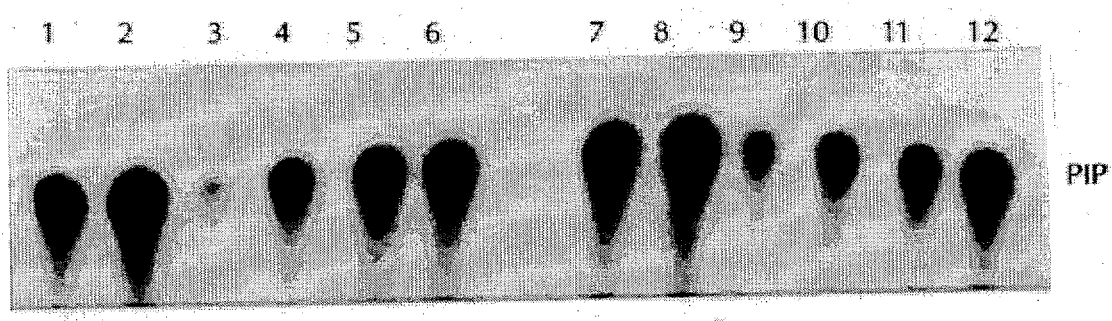
FIG. 17A presents work on immunoprecipitation of cells (Sf9), infected with complexes of p85/p110.
Figure 17B:
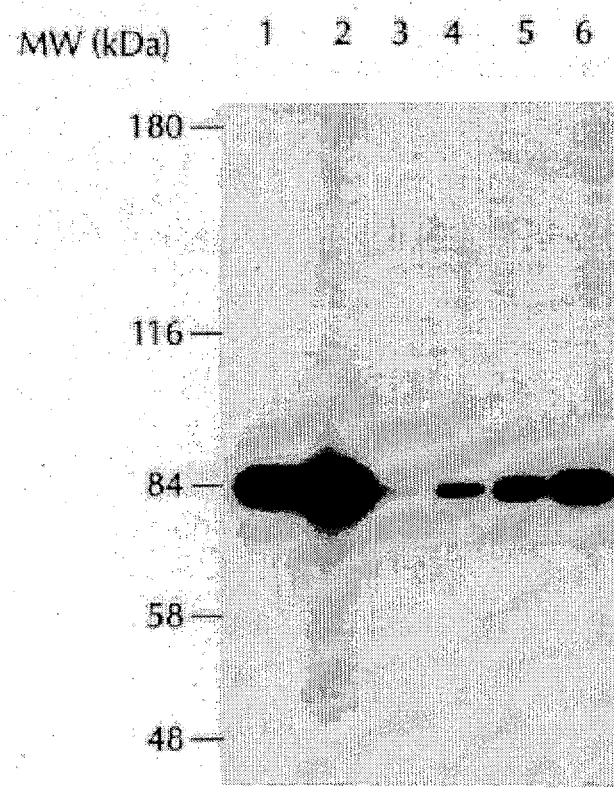
FIG. 17B parallels 17A, but with work involving p110 alone.
Figure 17C:
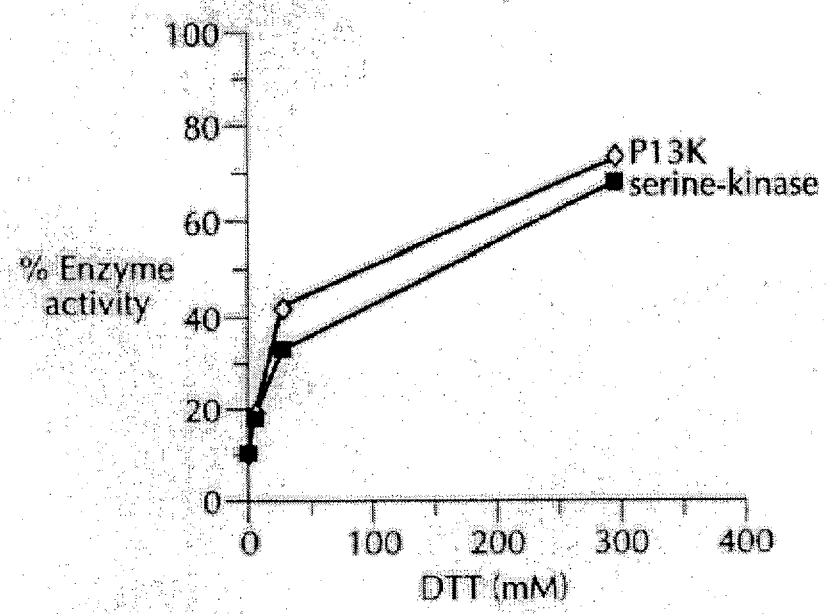
FIG. 17C shows the results of experiments designed to determine $NbS_2$ dose dependency.

Insect cells were infected with p85α/p110 complex, (see FIG. 17, A, lanes 1–6) or p110 alone, (see FIG. 17, B, lanes 7–12). The immunoprecipitates were washed twice with PI3-kinase buffer (20 mM Tris-HCl, pH 7.5, 100 mM NaCl, 0.5 mM EDTA). The samples were untreated or treated with 0.3 mM 5,5'-Dithio-bis [2-nitrobenzoic acid] ($Nbs_2$) for 15 minutes at 22° C. Excess reagent was removed by washing the complexes three times with PI3-kinase buffer and the immunoprecipitate was then incubated for 15 minutes at 22° C. with increasing concentrations of dithiothreitol (DTT). A control sample was incubated with DTT alone at a final concentration of 300 mM. The remaining DTT was removed by washing with lysis buffer and the immunoprecipitates were subjected to PI3-kinase assays or to in vitro protein kinase assays described below.

The experiment was carried out and the experimental results set forth in FIG. 17, A. In vitro PI3-kinase assays were performed on anti-p110 immunoprecipitates of these cells that had been treated as follows: untreated (see FIG. 17, A, lane 1 and 7); 300 mM DTT (lanes 2 and 8); treated with 0.3 mM $Nbs_2$ (lanes 3 and 9); immunoprecipitates pretreated with 0.3 mM $Nbs_2$ incubated with 3 mM DTT (lanes 4 and 10), 30 mM DTT (lanes 5 and 11); 300 mM DTT (lanes 6 and 12).

A further experiment to determine in vitro kinase activity with treatment of $Nbs_2$ and DTT was also conducted. Lysates of Sf9 cells that had been coinfected with p85α/p110 baculoviruses were also treated as follows: the lysates were immunoprecipitated with anti-p110 antibodies and treated as follows: untreated (see FIG. 17, B, lane 1); 300 mM DTT (lane 2); 0.3 mM $Nbs_2$ (lane 3); pretreated with 0.3 mM $Nbs_2$ and then incubated with 3 mM DTT, 30 mM DTT, 300 mM DTT (lanes 4, 5, 6 respectively). Samples were then subjected to in vitro kinase assays and analysis by SDS-PAGE was conducted. Phosphorylated proteins were visualized by autoradiography. The results are set forth in FIG. 17, B.

Approximately 95% of the PI3-kinase activity was lost when the samples were incubated with 0.3 mM $Nbs_2$, see FIG. 17, A, lanes 3 and 9, and a similar loss of protein serine kinase activity was also observed, see FIG. 17, B, lane 3. Both catalytic activities could be restored by incubating the modified enzyme with increasing concentrations of DTT, see FIG. 17, A, lanes 4–6 and 10–12; FIG. 17, B, lanes 4–6. Incubation of either the PI3-kinase complex or p110 with DTT alone at a final concentration of 300 mM, produced a slight activation of both the PI3-kinase activity, see FIG. 17, A, lanes 2 and 8 and the protein serine kinase activity, see FIG. 17, B, lane 2.

An additional experiment was carried out to determine the relative dose dependency of $Nbs_2$ and DTT treatment. FIG. 17, C, sets forth the dose curves for inactivation by $Nbs_2$, and reactivation with increasing concentrations of DTT, for both kinase activities. Both inactivation by $Nbs_2$, and reactivation by DTT, showed essentially identical dose response-curves for both protein kinase activities, see FIG. 17, C.

The loss of activity is likely due to the formation of a disulphide bond between an essential cysteine residue and thionitrobenzoate ($Nbs^-$) anion(s) in the catalytic domain.

EXAMPLE 16

Figure 18A:
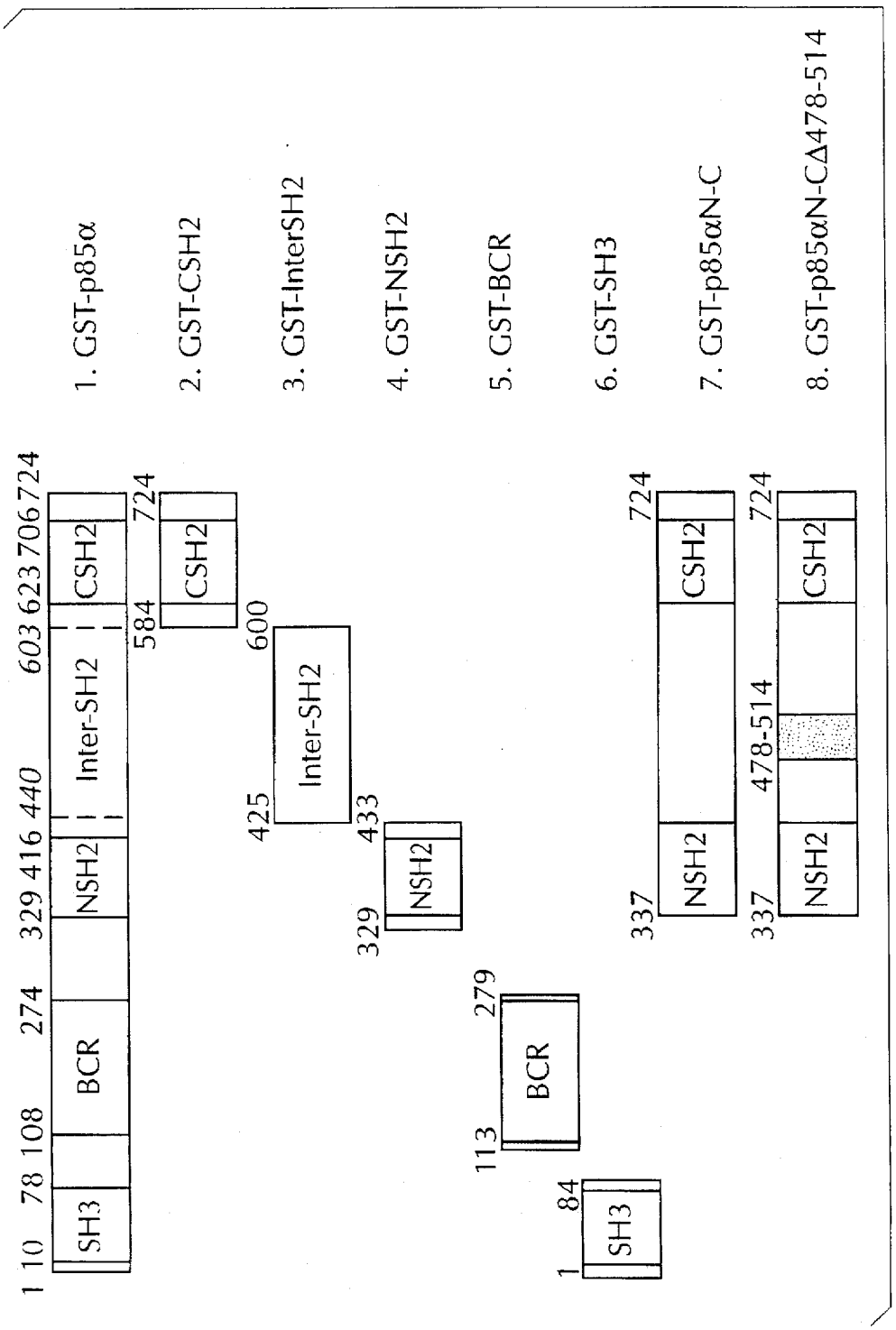
FIG. 18A depicts fusion proteins formed from GST and p85β sub-domains.
Figure 18B:
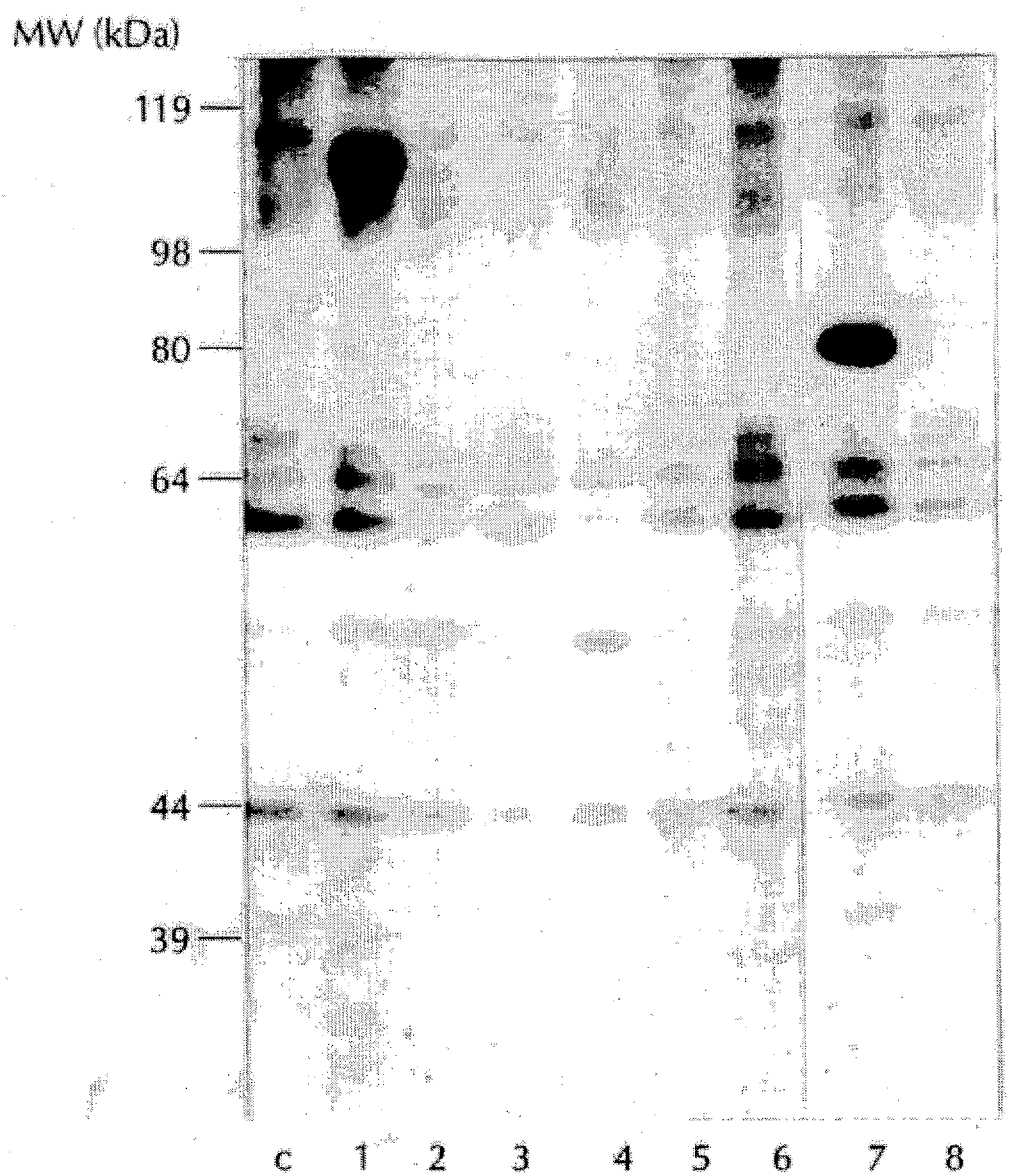
FIG. 18B shows the results of a kinase assay following mixing of the fusion proteins with p110.

Tests were also conducted to determine whether binding of the p85α protein to p110 was a prerequisite for p85 to act as a substrate for the protein-serine kinase activity. Various GST fusion proteins of subdomains of p85α were utilized as potential substrates for the protein serine kinase activity. The methods to prepared the GST fusion proteins is set forth in greater detail in Dhand, Dual Specificity, infra. (1993). The specific GST fusion proteins are set forth in FIG. 18, A.

The p110 protein was immunoprecipitated from insect cells, and equal amounts of each GST fusion protein or the GST protein alone, were mixed with p110 and the proteins were allowed to phosphorylate in vitro. The protein kinase assays were performed as described in Hiles et al., 1992, except the kinase buffer used contained 50 mM HEPES, pH 7.4, 150 mM NaCl, 5 mM EDTA, 10 mM $MnCl_2$, 0.02% Triton X-100, 10% glycerol. Phosphorylated proteins were analyzed by SDS-PAGE and autoradiography. The results of this experiment was set forth in FIG. 18, B.

The region of p85α responsible for binding to p110 includes amino acid residues 478–514, because the deletion mutant p85αN—CΔ478–514 is rendered totally unable to bind p110 or PI3-kinase activity when compared to a similar construct absent the deletion. Experiments conducted (data not shown) show that the only proteins that were phosphorylated by p110 were those to which it had been shown to bind. Only the full length p85α and the p85αN—C domain which includes the amino (N) and carboxy (C) terminal SH2 domain and the region in between were found to be phosphorylated by p110. The inter-SH2 domain is known to bind PI3-kinase activity, but was not phosphorylated in this assay. See example 5 supra.

These results can be explained if the in vitro phosphorylation sites for the kinase reside within one of the two adjacent SH2 domains or in the regions flanking the inter-SH2 domain. This data suggests that the protein-serine kinase activity of p110 can only be detected upon high affinity binding of p110 with its specific substrate p85 because the presence of the various unbound subdomains of p85 alone is not sufficient for phosphorylation to take place.

EXAMPLE 17

Phosphoamino acid analysis of the p85α subunit which was purified from Sf9 cells infected with p85α/p110 expressing baculovirus showed that the subunit contained phosphoserine. In order to identify the phosphorylation site on p85α in mammalian cells in vivo, the p85 subunit, phosphorylated both in vivo and in vitro, from a variety of sources was used. Phosphopeptide mapping was performed on purified PI3-kinase, using a $Y_{751}$ phosphopeptide column, from Sf9 and SGBAF-1 cells which were labelled with phosphate in vivo.

The SGBAF-1 cell line was established by transfection of bovine adrenal cortex zona faciculata cells with pSV3neo, as previously described for other cell types, Whitley et al., 1987. SGBAF-1 cells were maintained in Dulbecco's modified Eagles medium (DMEM) containing 10% FCS, 10 i.u. of penicillin/ml and 10 μm of streptomycin/ml. Maintenance of insect cell (Sf9) culture was carried out as previously described and as described in Summers and Smith, 1987.

The phosphorylation sites were labelled in vitro first by using PI3-kinase bound to a phosphopeptide column from Sf9 cells that had been coinfected with p85α and p110 viruses. Also bacterially expressed GST-p85α and GST-p85αN—C were bound to glutathione-sepharose beads and associated in vitro with p110 immunopurified from lysates of p110 infected Sf9 cells. The samples were resolved on SDS-PAGE gels, and the p85α protein identified by autoradiography was excised from the gel. Following trypsin digestion, the p85α protein digests were subjected to analysis by reverse-phase HPLC and radioactivity in the eluted fractions was detected by analyzing Cerenkov radiation.

Figure 19D:
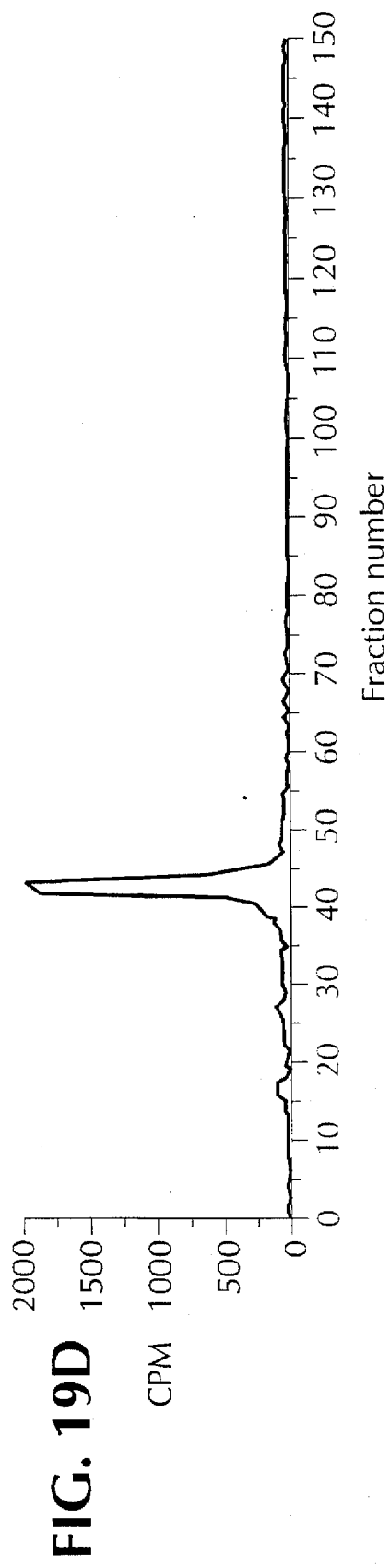
FIGS. 19A, B, C, D and E show various experiments designed to map for sites of phosphorylation by the protein.
Figure 19E:
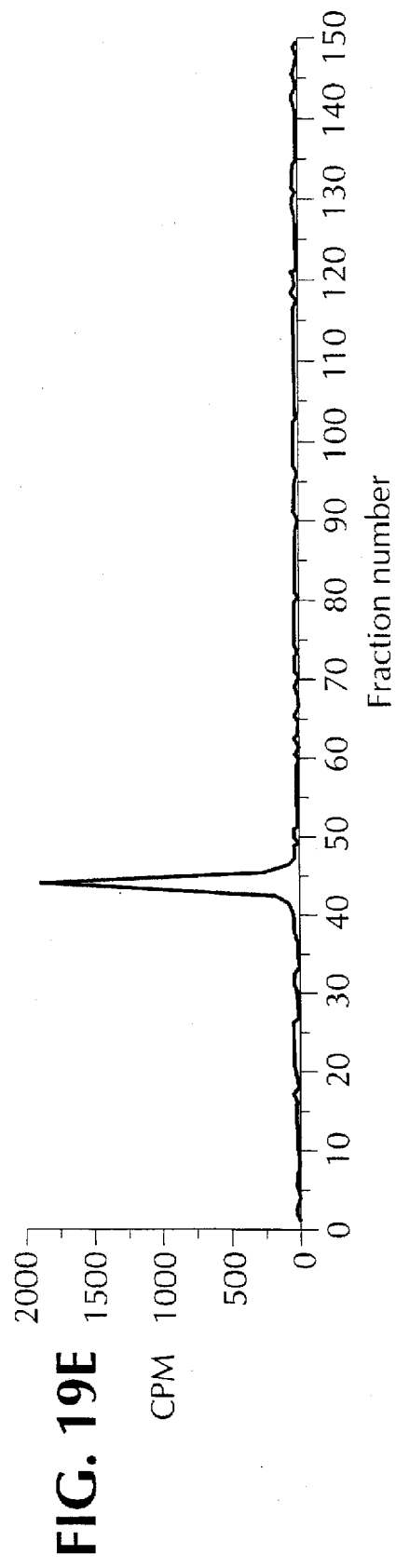
Figure 20A:
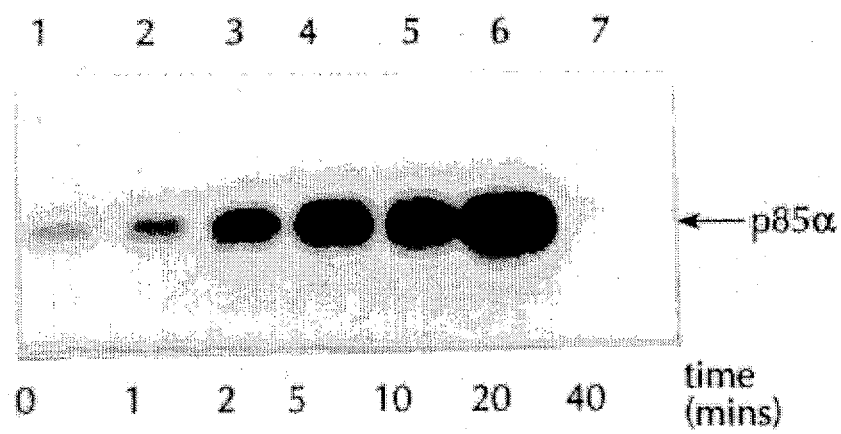
FIG. 20A shows immunoprecipitation of lysates of Sf9 transfectants, using p110 specific antibodies.
Figure 20B:
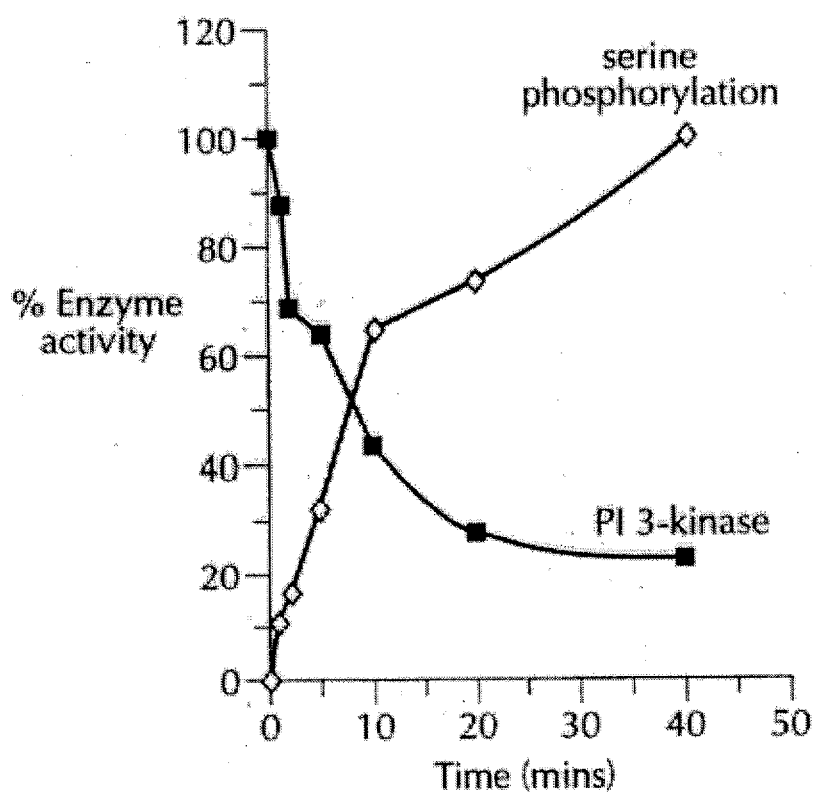
FIG. 20B depicts results from experiments showing a parallel between phosphorylation increase and PI3 kinase activity decrease.
Figure 20C:
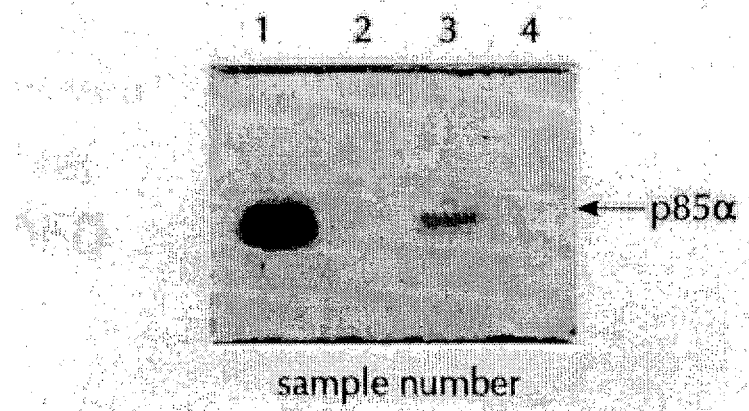
FIG. 20 shows that treating the enzymes with phosphatases inactivated them.
FIG. 20D shows restoration of activity.
Figure 20D:
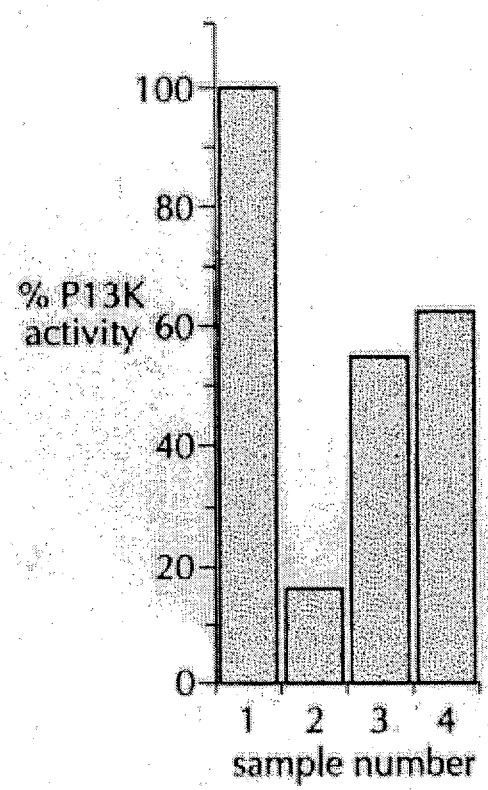

Specifically, the experiment conditions are as follows: Panel A: Phosphopeptide-purified PI3-kinase from Sf9 cells coinfected with p85α/p110 viruses and labelled with phosphate in vitro; B: PI3-kinase treated as above from SGAF-1 cells labelled with phosphate in vivo; C: Phosphopeptide-purified PI3-kinase from Sf9 cells coinfected with p85α/p110 viruses phosphorylated in vitro in the presence of [γ$^{32}$P] ATP. GST-p85α (panel D) and GST-p85αN—CSH2 (panel E) were bound to Glutathione-sepharose beads, and then incubated with p110 containing Sf9 cell lysates. Complexed proteins were phosphorylated in vitro in the presence of [γ$^{32}$P] ATP. The results set forth in FIG. 19 establish that the same major phosphopeptide was detected in maps of p85α from all different preparations, whether the proteins had been labelled in vitro or in vivo.

As the bacterial GSTp85αN—C phosphorylated in vitro by p110 and digested with trypsin contains the same phosphopeptide, this suggests that the phosphoserine residue resides in the C-terminal half of the p85 protein. The phosphopeptide was purified from a tryptic digest of a large scale preparation of p85 from Sf9 cells coinfected with p85α and p110 viruses, phosphorylated in vitro, and was then subjected to mass and N-terminal sequence analysis. Automated amino terminal Edman degradation identified the amino terminus of the phosphopeptide and suggested that it had the sequence KLNEWLGNENTEDQY SLVEDDEDLPHHDEK (SEQ ID NO: 5). Mass analysis revealed a mass of 3583 kDa which was consistent with a single phosphorylation site on this peptide since the mass of the peptide containing no phosphorylated residues should be 3484 kDa. Phosphoamino acid analysis indicated that the molecule was exclusively phosphorylated on serine in vitro, and these results establish that Ser-608 is the major site of phosphorylation. See example 10. Phosphothreonine was also detected in the phosphoamino acid analysis of Sf9 cells labelled in vivo, see FIG. 12, but it was not possible to recover a peptide containing a phosphothreonine residue.

EXAMPLE 18

The regulation of PI3-kinase can be achieved by the associated protein serine/threonine kinase.

Lysates of insect cells that have been coinfected with viruses expressing the p85α and the p110 proteins were immunoprecipitated with antibodies directed against the p110 subunit. The immunocomplexes were phosphorylated in the presence of [γ$^{32}$P] ATP for increasing periods of time for 0, 1, 2, 5, 10, 20 and 40 minutes, see FIG. 20, A, lanes 1–7. After each time period, the reaction was stopped by extensive washing with lysis buffer containing 10 mM EDTA to chelate and remove excess MnCl$_2$. These immunocomplexes were then divided into two portions and were used for analysis of proteins by SDS-PAGE and autoradiography (FIG. 20, A) and the remaining sample was subjected to PI3-kinase assay (FIG. 20, B).

FIG. 20, B, demonstrates that the increased level of phosphorylation observed on the p85α subunit is paralleled by a corresponding decrease in PI3-kinase activity. After 20 minutes incubation of the enzyme in the presence of MnCl$_2$ and [γ$^{32}$P] ATP, approximately 80% of the PI3-kinase activity is lost. This effect can be reversed with treatment of the inactivated enzyme with phosphatases. Treatment of the serine phosphorylated enzyme, see FIG. 20, C, lane 2, with either phosphoprotein phosphatase 2A, lane 3 or with alkaline phosphatase, lane 4 removed [γ$^{32}$P] ATP, from the p85α subunit. Parallel PI3-kinase assays of these phosphatase-treated samples revealed restoration of activity, see FIG. 20, D, lanes 1–4. Untreated PI3-kinase was also incubated with either alkaline phosphatase or phosphoprotein phosphatase 2A, but no significant change in PI3-kinase activity was observed.

Based on the above findings relating to the intersubunit binding regions and the associated PI3-kinase and serine kinase activities, antagonist and agonist molecules of this invention which operate to inhibit or potentiate the activities discussed previously, can be prepared and used to study the interaction of the p85 and p110 subunits by either mimicking the effect of the PI3-kinase (agonist) or by blocking the interaction of the subunits (antagonist). The antagonist molecules can take the form of antibodies raised against the specific binding regions which when contacted with the one subunit, i.e., p85, block the interaction with the other subunit, p110, as disclosed in this application. These antibodies can be monoclonal antibodies which are produced by preparing hybridoma cell lines according to conventional methods.

The antagonist can also be directed to the p85 subunit wherein the antagonist blocks the specific residues that participate in serine kinase phosphorylation. Especially preferred is an antagonistic molecule that binds or blocks the serine 608 residue of the p85 subunit as described previously. The antagonistic effects of these molecules suggest their utility in conditions characterized by excess or undesirable kinase activity.

It is also possible to prepare a nucleic acid molecule that hybridizes to and inhibits expression of the nucleic acid molecule that codes for the specific binding region, especially preferred would be a molecule that hybridizes to the nucleic acid sequence that codes for the inter SH2 region, and most preferred would be molecules that hybridizes to amino acid residues 445 to 485 of p85β and amino acid residue 478–513 of p85α.

The agonist molecules can be also be useful in situations where activity is lower than normal due to pathophysiological disorders. i.e., in cases of chemotherapy. An agonist preferably stimulates the phosphorylation of the p85 subunit at the serine residue at position 608, wherein phosphorylation at the serine residue inhibits PI3-kinase activity. The agonist preferably includes an amino acid sequence deduced from regions based on the conservation of sequences between different families of kinases.

After the antagonistic or agonistic molecules and their sequences have been identified, methods to express these specific molecules can be carried out by preparing vectors containing the specific sequences, i.e., plasmids, transfecting cells to express the molecules incorporated therein.

Therefore, in summary, it has been demonstrated by the above that by inhibiting binding between the p85 and p110 subunits, it is possible to modulate PI3-kinase activity. By also manipulating or disabling the DRHNSN sequence of the p110 subunit, the protein serine kinase activity of p110 can be affected. An increase in serine kinase activity also results in lowering PI3-kinase activity. An agonist for a ligand increases serine kinase activity by binding to the p85 subunit and stimulates phosphorylation of the p85 subunit. Such an agonist probably provides an increased amount of serine kinase activity in vivo or binds to the p85 subunit more efficiently. Preferably this agonist includes at least a portion of the sequence which corresponds to the catalytic domain of the p110 subunit.

The discovery of the specific binding region and the novel serine kinase activity residing in a specific region provides tremendous potential in providing therapeutic/diagnostic aids and assays, to control PI3-kinase activity and to manipulate signal transduction pathways. Moreover, a method to alter the serine 608 residue of the p85 subunit also provides a means to inhibit serine kinase activity, The alteration can be carried out by known methods, i.e., site-directed, target mutation, deletion, or other means known to those skilled in this art.

Additionally, the methods to inhibit binding between the subunits and to inhibit the serine kinase ability of the p110 subunit, in addition to the elucidation of the primary structure of the subunit allows for the identification of agonist and antagonists for ligands that bind to the subunits. The agonist and antagonist, in addition to the nucleic acid molecules which code for the (ant)agonists, the expression vectors, such as, but not limited to, the baculovirus vectors, containing the nucleic acid molecules are also provided herein. An expression vector or plasmid for expressing the nucleic acid molecules are also intended.

In addition, an antisense nucleic acid molecule which hybridizes to a nucleic acid molecule which codes for an antagonist including the inter-SH2 region of the p85 subunit can be utilized to inhibit its expression. In this way, the binding of the p85 to its p110 catalytic domain is inhibited.

Further provided herein are the cells or cell lines which may be transfected with the vector, where the cells can be derived from eukaryotic and mammalian cells. Specifically, the baculovirus expression system in Sf9 cells transfected with agonist molecule is but one example.

In addition, the invention also provides for a molecule or an antibody that interferes with the binding between the subunits.

Another aspect of the invention is a pharmaceutical formulation comprising an (ant)agonist formulated for pharmaceutical use, optionally together with an acceptable adjuvant, diluent, carrier or excipient and/or in unit dosage form. Conventional pharmaceutical practice may be employed to provide suitable formulations or compositions.

Thus, the formulations of this invention can be applied to parenteral administration, for example, intravenous, subcutaneous, intramuscular, intraorbital, opthalmic, intraventricular, intracranial, intracapsular, intraspinal, intracisternal, intraperitoneal, topical, intranasal, aerosol, scarification, and also oral, buccal, rectal or vaginal administration.

The formulations of this invention may also be administered by the transplantation into the patient of host cells expressing the nucleic acid molecules of the instant invention or by the use of surgical implants which release the formulations of the invention. The transplantation can also be performed at the specific tumor site.

Parenteral formulations may be in the form of liquid solutions or suspensions; for oral administration, formulations may be in the form of tablets or capsules; and for intranasal formulations, in the form of powders, nasal drops, or aerosols.

Methods well known in the art for making formulations are to be found in, for example, "Remington's Pharmaceutical Sciences."

In general terms, the (ant)agonist protein fragments of this invention may be provided in an aqueous physiological buffer solution containing about 0.1 to 10% w/v compound for parenteral administration. General dose ranges are from about 1 mg/kg to about 1 g/kg of body weight per day; a preferred dose range is from about 0.01 mg/kg to 100 mg/kg of body weight per day. The preferred dosage to be administered is likely to depend upon the type and extent of progression of the condition being addressed, the overall health of the patient, the make up of the formulation, and the route of administration.

These antagonist and agonist molecules also provide a means to screen molecules in samples for the presence of the p85 protein. This method entails contacting a known amount of the (ant)agonist of the invention and an amount of the sample protein and measuring the binding of any p85 protein present in the sample to said (ant)agonist.

A further aspect of the invention is use of the agonist to treat subjects with pathological conditions characterized by insufficient PI3-kinase activity. In addition to comprising an agonist for PI3-kinase activity, the composition can contain a carrier, adjuvant, diluent, excipient, which facilitates the incorporation of the agonist. An (ant)agonist which competes with the p110 subunit for binding to the p85 subunit is also intended.

The study of the structure of the p85 and p110 subunits and their interaction, using art known techniques can lead to the design of molecules which mimic the action of the p110 fragment.

It is believed that other embodiments may be incorporated into the present invention without departing from the spirit and scope of the invention. It is not intended that the present invention be limited to only the described embodiments. Modification of these embodiments will be recognized by those skilled in the art. Rather, the invention should be circumscribed by the scope of the appended claims.

REFERENCES

1. Backer, J. M. et al., (1992), EMBO J, 11, 3469–3479.
2. Bernstein, F. C. et al, (1977), J. Mol. Biol. 112, 535–542.
3. Bjorge, J. D. et al., (1990), PNAS, USA, 87, 3816–3820.
4. Cantley, L. C. et al., (1991), Cell 64, 281–302.
5. Carpenter, C. L. et al., (1993), J. Bio. Chem., 268, 9478–83.
6. Carpenter, C. L. et al., (1990), J. Biol. Chem., 265, 19704–19711.
7. Carpenter, C. L. et al., (1991), Mol. & Cell Biol. 13 (3): 1657–1665 (1993).
8. Chan, T. O. et al., (1990), Mol. Cell. Biol. 10, 3280–3283.
9. Cohen, B. et al., (1987), Biochemistry 26, 6845–6852.
10. Cohen, B. et al., (1990), Mol. Cell. Biol. 10, 2909–2915.
11. Conway, J. F. et al., (1990), Int. J. Biol. Macromol., 12, 328–334.
12. Coughlin, S. R. et al., (1987), Science 243, 1191–1194.
13. Courtneidge, S. A. et al., (1987), Cell 50, 1031–1037.
14. Eliopoulos, E. G. (1989), Documentation for Leeds Prediction Programs, Department of Biophysics, University of Leeds.
15. End, P. et al., (1993), J. Biol. Chem. 268, 10066–10075.
16. Enderman, G. et al., (1987), Biochemistry 26, 6845–6852.
17. Escobedo, J. A. et al., (1991), Mol. Cell. Biol. 11, 1125–1132.
18. Escobedo, J. A. et al., (1991b), Cell 65, 75–82.
19. Escobedo, J. A. et al., (1993), J. Biol. Chem. 268, 10066–10075.

20. Fantl, W. J. et al., (1992), Cell, 69, 413–423.
21. Fry, M. J., (1992), Current Biol., 2, 78–80.
22. Fry, M. J. et al., (1992), Biochem. J., 288, 383–393.
23. Fukui, Y. et al., (1989), Mol. Cell. Biol. 9, 1651–1658.
24. Giorgetti, S., et al., (993), J. Biol. Chem., 268, 7358–7364.
25. Gout, I. et al., (1992), Biochem., J. 288, 395–405.
26. Graziani, A. et al., (1991), J. Biol. Chem. 226, 22087–22090.
27. Hanks, S. K. et al. (1988), Science 241, 42–52.
28. Hara, K. et al., (1993), "Insulin-stimulated association of P13-kinase activity with IRS-1 is required for the accumulation of PtdIns (3,4,5)P$_3$ and the stimulation of glucose transport".
29. Herman, P. K. et al., (1990), Mol. Cell. Biol., 10, 6742–6754.
30. Hiles, I. D. et al., (1992), Cell, 70, 419–429.
31. Hodges, R. S. et al., (1972), Cold Spring Harbor Symp. Quant. Biol., 37, 299–310.
32. Hou, W. M. et al., (1988), Biochem. Biophys. Acta., 959, 67–75.
33. Jamey, P. A. et al., (1992) J. Biol. Chem 267–11818–11823.
34. Kaplan, D. R. (1987), Cell, 50, 1021–1029.
35. Kaplan, D. R. et al., (1990), Cell, 61, 125–133.
36. Krypta, R. M. et al., (1990), Cell 62, 481–492.
37. Kunz, J. et al., (1993), Cell, 73, 585–596.
38. Maru, Y. et al. (1991), Cell 67, 459–468.
39. McLachlan, A. D. et al., (1975), J. Mol. Biol., 98, 293–304.
40. Meisenhelder, J. et al., (1989), Cell 57, 1109–1122.
41. Morgan, S. J. et al. (1990), Eur. J. Biochem., 191, 761–767.
42. Morrison, D. K. et al., (1989), Cell, 58, 649–657.
43. Muirhead, H. et al., (1986), EMBO J, 5, 475–481.
44. Otsu, M. et al., (1991), Cell, 65, 91–104.
45. Panayotou, G. et al., (1992), EMBO J, 11, 4261–4272.
46. Panayotou, G. et al., (1992), Trends in cell biol. 2, 358–360.
47. Panayotou, G. et al. (1993), Bioessays 15, 171–177.
48. Parry, D. A. D., (1975), J. Mol. Biol, 98, 519–535.
49. Pawson, T. et al., (1992), Cell, 71, 359–362.
50. Pawson, T. et al., (1993), Current Biology, 3, 434, 442.
51. Pawson, T. (1992), Current opinion in structural biology 2, 432–437.
52. Philips, G. N. et al., (1979), Nature (London), 278, 413–417.
53. Philips, G. N. Fillers, J. P., Cohen, C. (1979), Nature (London).
54. Reif, K. et al., (1993), J. Biol. Chem., 268, 10780–10788.
55. Roche, S. et al., (1993), J. Biol. Chem. in press.
56. Ruderman, N. B. et al., (1990), PNAS, USA, 87, 1411–1415.
57. Ruiz-Larrea, F. et al., (1993), Biochem J. 290, 609–616.
58. Saraste, M. et al., (1990), Trends Biochem. Sci. 15, 430–434.
59. Scholz, G. et al., (1991), J. Biochem. 201, 249–255.
60. Schu, P. V. et al., (1993), Science 260, 88–91.
61. Shibasaki, F. et al., (1991), J. Biol. Chem. 266, 8108–8114.
62. Shibasaki, F. et al., (1991), J. Biol. Chem. 266, 8108–8114.
63. Skolnik, E. Y. et al., (1991), Cell 65, 83–90.
64. Smith, D. B. et al., (1988), Gene 67, 31–40.
65. Summers, M. D. et al., (1987), "A Manual of Methods For Baculovirus Vectors and Insect Cell Culture Procedures", Vol. 1555.
66. Takebe, Y. et al., (1988), Mol. Cell, Biol. 8, 466–472.
67. Taylor, S. S. (1992), Annu Rev Cell Biol 8, 429–462.
68. Ullrich, A. et al., (1990), Cell 61, 203–212.
69. Valius, M. et al., (1993), Cell, 73, 321–334.
70. Varticovski, L. et al., (1989), Nature 342, 3895–3904.
71. Varticovski, L. et al., (1991), Mol. Cell. Biol. 11, 1107–1103.
72. Whitley, G. et al., (1987), Mol. Cell. Endocrinol. 52, 279–284.
73. Whitman, M. et al., (1985), Nature 315, 239–242.
74. Whitman, M. et al., (1987), Biochem. J. 247, 165–174.
75. Whitman, M. et al., (1988), Biochem. Biophys. Acta. 948, 327–344.
76. Whitman, M. et al., (1988), Nature, 332, 644–646.
77. Yonezawa, K., (1992), J. Biol. chem. 267, 25958–25965.
78. Yu, F. X. et al., (1992), J. Biol. Chem. 267, 14616–14621.
79. Yu, J. C. et al. (1991), Mol. Cell Biol. 11, 3781–3785.

We claim:

1. Method for inhibiting the serine kinase ability of phosphatidyl-inositol 3 kinase (Pi3-kinase) which comprises disabling the sequence DRHNSN in the p110 subunit of phosphatidyl-inositol 3 kinase (PI3-kinase).

2. Method of claim 1, wherein said sequence is disabled by targeted mutation.

3. Method of claim 1, wherein said sequence is disabled by interaction with a molecule which inhibits serine kinase function.

4. Method of claim 3, wherein said molecule is an antibody which specifically binds to said DRHNSN sequence.

5. Method of claim 3, wherein said molecule is a monoclonal antibody which specifically binds said DRHNSN sequence.

6. Method to inhibit binding between p85 and p110 subunits of PI3-kinase comprising disabling the inter-SH2 region of said p85 subunit of said PI3-kinase.

7. Method of claim 6, comprising disabling a region comprising amino acid residue 445 to amino acid residue 485 of p85β subunit of said PI3-kinase.

8. Method of claim 6, comprising disabling a region containing amino acid residue 478 to amino acid residue 513 of p85α subunit of said PI3-kinase.

9. Isolated antagonist for a ligand which binds to the p85 subunit of PI3-kinase, wherein binding of said antagonist to said p85 subunit, prevents phosphorylation at position 608 which is serine, and results in a decrease in PI3-kinase activity, wherein said antagonist comprises an amino acid sequence which corresponds to a disabled DRHNSN sequence.

10. An isolated antibody that specifically binds to a p85 subunit of PI3-kinase at an epitope located in the inter-SH2 region of said p85 subunit, wherein said antibody interferes with binding between said p85 and p110 subunit of said PI3-kinase.

11. The isolated antibody of claim 10, wherein said antibody specifically binds to an epitope comprising at least amino acid residue 445 to amino acid residue 485 of said p85β subunit of said PI3-kinase.

12. The isolated antibody of claim 10, wherein said antibody specifically binds to an epitope comprising at least amino acid residue 478 to amino acid residue 513 of p85α subunit of said PI3-kinase.

13. The antibody of claim 10, wherein said antibody is a monoclonal antibody.

14. Hybridoma cell line which produces antibody of claim 10.

15. Method to inhibit binding between p85 and p110 subunits of PI3-kinase, comprising contacting a sample containing p85 with an antibody of claim 10.

16. Method to inhibit the serine kinase ability of PI3-kinase enzyme comprising disabling or interfering with the serine residue at position 608 of a p85 subunit of said PI3-kinase enzyme.

17. Method of claim 16, wherein said serine residue is disabled by targeted mutation.

18. Isolated agonist for a ligand which binds to the p85 subunit of PI3-kinase, wherein binding of said agonist to said p85 subunit stimulates phosphorylation at amino acid residue position 608, which is serine, of said p85 subunit, and increases serine kinase activity of said PI3-kinase, wherein said agonist comprises at least a domain having PI3-kinase catalytic activity corresponding to a region of the p110 subunit of said PI3-kinase exhibiting said PI3-kinase activity.

19. Isolated nucleic acid molecule coding for the agonist of claim 18.

20. Plasmid containing the nucleic acid molecule of claim 19.

21. Cell line transfected with the nucleic acid molecule of claim 19, which expresses a protein encoded by said nucleic acid molecule.

22. Cell line transfected with the plasmid of claim 23, which expresses a protein encoded by said nucleic acid molecule.

23. Cell line of claim 21, wherein said cell line is a eukaryotic cell line.

24. Molecule which binds to the p85 subunit of PI3-kinase, wherein binding of said molecule to said subunit protects prior phosphorylation of said subunit at amino acid residue at position 608, which is serine, and results in decreasing PI3-kinase activity.

25. Molecule of claim 24, wherein said molecule is an antibody.

26. Molecule of claim 25, wherein said antibody is a monoclonal antibody.

27. Hybridoma cell line which produces the monoclonal antibody of claim 26.

28. Method for the manufacture of a medicament to inhibit PI3-kinase activity, which comprises selecting a substance which is capable of binding to or otherwise interfering with the sequence DRHNSN of the p110 subunit of PI3-kinase enzyme and formulating said substance for medical use.

* * * * *